(12) United States Patent
Bloom et al.

(10) Patent No.: US 9,427,281 B2
(45) Date of Patent: Aug. 30, 2016

(54) BRONCHOSCOPE-COMPATIBLE CATHETER PROVIDED WITH ELECTROSURGICAL DEVICE

(75) Inventors: Eliot Bloom, Hopkinton, NH (US); Donald Earles, Portsmouth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 923 days.

(21) Appl. No.: 13/048,735

(22) Filed: Mar. 15, 2011

(65) Prior Publication Data
US 2012/0232553 A1    Sep. 13, 2012

Related U.S. Application Data

(60) Provisional application No. 61/452,073, filed on Mar. 11, 2011.

(51) Int. Cl.
*A61B 18/14*    (2006.01)
*A61B 18/00*    (2006.01)

(52) U.S. Cl.
CPC ... *A61B 18/1492* (2013.01); *A61B 2018/00172* (2013.01); *A61B 2018/00178* (2013.01);
(Continued)

(58) Field of Classification Search
CPC .... A61B 18/12; A61B 18/14; A61B 18/1402; A61B 18/1477; A61B 18/148; A61B 18/1482; A61B 18/485; A61B 18/1487; A61B 18/149; A61B 18/1492; A61B 2018/0091; A61B 2018/00916; A61B 2018/00922; A61B 2018/0094; A61B 2018/00946; A61B 2018/00952; A61B 2018/00958; A61B 2018/00541
USPC ......................................................... 606/46
See application file for complete search history.

(56) References Cited

U.S. PATENT DOCUMENTS 2,888,928 A    6/1959  Seiger
3,682,130 A    8/1972  Jeffers
(Continued)

FOREIGN PATENT DOCUMENTS

WO    WO96/04955 A2    2/1996
WO    WO2007-037785    4/2007
(Continued)

OTHER PUBLICATIONS

Swedish Medical Center, Update, http://www.swedish.org/Media-Files/Documents/HealthProfessionals/PhysPractice-Magazine/PPSEPT10, Sep. 2010, 7 pages.
(Continued)

*Primary Examiner* — Jaymi Della
*Assistant Examiner* — Eunhwa Kim
(74) *Attorney, Agent, or Firm* — Christopher & Weisberg, P.A.

(57)    ABSTRACT

A catheter system can include an electrical adapter and a catheter. The electrical adapter includes a hollow adapter body having a longitudinally extending channel and an electrical terminal positioned within the channel. The electrical adapter can be configured to connect to an energy source. The catheter can include an elongated body having a proximal end portion and a distal end portion, and an electrical connector coupled to the proximal end portion. The electrical connector forms the outer periphery of the catheter along a portion of the longitudinal length of the catheter. The electrical terminal and the electrical connector contact each other when the electrical connector is advanced through the channel to an electrical contact position in the channel, and are isolated from each other when the electrical connector is proximal of the electrical contact position.

14 Claims, 12 Drawing Sheets

(52) U.S. Cl.
CPC .......... *A61B2018/00541* (2013.01); *A61B 2018/00601* (2013.01); *A61B 2018/1475* (2013.01); *A61B 2218/007* (2013.01)

(56) References Cited

U.S. PATENT DOCUMENTS

| | | | |
|---|---|---|---|
| 3,750,650 A | 8/1973 | Ruttgers | |
| 4,060,088 A | 11/1977 | Morrison, Jr. et al. | |
| 4,195,637 A | 4/1980 | Gruntzig et al. | |
| 4,207,897 A | 6/1980 | Lloyd et al. | |
| 4,244,371 A | 1/1981 | Farin | |
| 4,248,224 A | 2/1981 | Jones | |
| 4,275,734 A | 6/1981 | Mitchiner | |
| 4,276,874 A | 7/1981 | Wolvek et al. | |
| 4,278,090 A | 7/1981 | van Gerven | |
| 4,321,931 A | 3/1982 | Hon | |
| 4,342,218 A | 8/1982 | Fox | |
| 4,355,642 A | 10/1982 | Alferness | |
| 4,377,168 A | 3/1983 | Rzasa et al. | |
| 4,381,007 A | 4/1983 | Doss | |
| 4,519,389 A | 5/1985 | Gudkin et al. | |
| 4,598,698 A | 7/1986 | Siegmund | |
| 4,601,290 A | 7/1986 | Effron et al. | |
| 4,671,274 A | 6/1987 | Scrochenko | |
| 4,736,749 A | 4/1988 | Lundback | |
| 4,779,611 A | 10/1988 | Grooters et al. | |
| 4,919,129 A | 4/1990 | Weber et al. | |
| 4,931,047 A | 6/1990 | Broadwin et al. | |
| 4,932,952 A | 6/1990 | Wojciechowicz, Jr. | |
| 4,943,290 A | 7/1990 | Rexroth et al. | |
| 4,950,232 A | 8/1990 | Ruzicka et al. | |
| 4,985,030 A | 1/1991 | Melzer et al. | |
| 4,998,933 A | 3/1991 | Eggers et al. | |
| 5,047,027 A | 9/1991 | Rydell | |
| 5,047,028 A | 9/1991 | Qian | |
| 5,190,541 A | 3/1993 | Abele et al. | |
| 5,195,959 A | 3/1993 | Smith | |
| 5,197,963 A | 3/1993 | Parins | |
| 5,254,117 A | 10/1993 | Rigby et al. | |
| 5,281,215 A | 1/1994 | Midler | |
| 5,287,845 A * | 2/1994 | Faul et al. ............... | 600/135 |
| 5,309,896 A | 5/1994 | Moll et al. | |
| 5,316,000 A | 5/1994 | Chapelon et al. | |
| 5,317,878 A | 6/1994 | Bradshaw et al. | |
| 5,318,525 A | 6/1994 | West et al. | |
| 5,322,520 A | 6/1994 | Milder | |
| 5,323,781 A | 6/1994 | Ideker et al. | |
| 5,324,255 A | 6/1994 | Passafaro et al. | |
| 5,324,284 A | 6/1994 | Imran | |
| 5,324,286 A | 6/1994 | Fowler | |
| 5,330,521 A | 7/1994 | Cohen | |
| 5,334,181 A | 8/1994 | Rubinsky et al. | |
| 5,334,193 A | 8/1994 | Nardella | |
| 5,336,220 A | 8/1994 | Ryan et al. | |
| 5,348,554 A | 9/1994 | Imran et al. | |
| 5,353,783 A | 10/1994 | Nakao et al. | |
| 5,354,258 A | 10/1994 | Dory | |
| 5,361,752 A | 11/1994 | Moll et al. | |
| 5,372,603 A | 12/1994 | Acker et al. | |
| 5,383,874 A | 1/1995 | Jackson et al. | |
| 5,385,148 A | 1/1995 | Lesh et al. | |
| 5,395,312 A | 3/1995 | Desai | |
| 5,396,887 A | 3/1995 | Imran | |
| 5,397,304 A | 3/1995 | Truckai | |
| 5,400,770 A | 3/1995 | Nakao et al. | |
| 5,400,783 A | 3/1995 | Pomeranz et al. | |
| 5,401,272 A | 3/1995 | Perkins | |
| 5,403,309 A | 4/1995 | Coleman et al. | |
| 5,403,311 A | 4/1995 | Abele et al. | |
| 5,405,376 A | 4/1995 | Mulier et al. | |
| 5,409,483 A | 4/1995 | Campbell et al. | |
| 5,417,709 A | 5/1995 | Slater | |
| 5,423,807 A | 6/1995 | Mlilder | |
| 5,423,811 A | 6/1995 | Imran et al. | |
| 5,427,119 A | 6/1995 | Swartz et al. | |
| 5,431,168 A | 7/1995 | Webster, Jr. | |
| 5,431,649 A | 7/1995 | Mulier et al. | |
| 5,433,708 A | 7/1995 | Nichols et al. | |
| 5,435,308 A | 7/1995 | Gallup et al. | |
| 5,437,651 A | 8/1995 | Todd et al. | |
| 5,441,503 A | 8/1995 | Considine et al. | |
| 5,443,463 A | 8/1995 | Stern et al. | |
| 5,443,470 A | 8/1995 | Stern et al. | |
| 5,445,638 A | 8/1995 | Rydell et al. | |
| 5,450,843 A | 9/1995 | Moll et al. | |
| 5,452,582 A | 9/1995 | Longsworth | |
| 5,452,733 A | 9/1995 | Sterman et al. | |
| 5,460,629 A * | 10/1995 | Shlain et al. ............... | 606/46 |
| 5,462,545 A | 10/1995 | Wang et al. | |
| 5,465,717 A | 11/1995 | Imran et al. | |
| 5,469,853 A | 11/1995 | Law et al. | |
| 5,472,876 A | 12/1995 | Fahy | |
| 5,478,309 A | 12/1995 | Sweezer et al. | |
| 5,478,330 A | 12/1995 | Imran et al. | |
| 5,486,193 A | 1/1996 | Bourne et al. | |
| 5,487,385 A | 1/1996 | Avitall | |
| 5,487,757 A | 1/1996 | Truckai et al. | |
| 5,490,819 A | 2/1996 | Nicholas et al. | |
| 5,496,271 A | 3/1996 | Burton et al. | |
| 5,496,312 A | 3/1996 | Klicek | |
| 5,497,774 A | 3/1996 | Swartz et al. | |
| 5,498,248 A | 3/1996 | Milder | |
| 5,500,012 A | 3/1996 | Brucker et al. | |
| 5,505,730 A | 4/1996 | Edwards | |
| 5,516,505 A | 5/1996 | McDow | |
| 5,520,682 A | 5/1996 | Baust et al. | |
| 5,522,870 A | 6/1996 | Ben-Zion | |
| 5,536,267 A | 7/1996 | Edwards et al. | |
| 5,540,679 A | 7/1996 | Fram et al. | |
| 5,542,916 A | 8/1996 | Hirsch et al. | |
| 5,542,945 A | 8/1996 | Fritzsch | |
| 5,545,195 A | 8/1996 | Lennox et al. | |
| 5,545,200 A | 8/1996 | West et al. | |
| 5,549,604 A | 8/1996 | Sutcu | |
| 5,555,883 A | 9/1996 | Avitall | |
| 5,556,397 A | 9/1996 | Long et al. | |
| 5,558,671 A | 9/1996 | Yates | |
| 5,560,362 A | 10/1996 | Sliwa, Jr. et al. | |
| 5,562,720 A | 10/1996 | Stern et al. | |
| 5,569,241 A | 10/1996 | Edwards | |
| 5,569,243 A | 10/1996 | Kortenbach et al. | |
| 5,571,088 A | 11/1996 | Lennox et al. | |
| 5,571,215 A | 11/1996 | Sterman et al. | |
| 5,573,424 A | 11/1996 | Poppe | |
| 5,573,532 A | 11/1996 | Chang et al. | |
| 5,575,766 A | 11/1996 | Swartz et al. | |
| 5,575,788 A | 11/1996 | Baker et al. | |
| 5,575,810 A | 11/1996 | Swanson et al. | |
| 5,578,007 A | 11/1996 | Imran | |
| 5,582,609 A | 12/1996 | Swanson et al. | |
| 5,588,432 A | 12/1996 | Crowley | |
| 5,590,657 A | 1/1997 | Cain et al. | |
| 5,595,183 A | 1/1997 | Swanson et al. | |
| 5,599,346 A | 2/1997 | Edwards et al. | |
| 5,607,422 A | 3/1997 | Smeets et al. | |
| 5,607,462 A | 3/1997 | Imran | |
| 5,617,854 A | 4/1997 | Munsif | |
| 5,630,837 A | 5/1997 | Crowley | |
| 5,637,090 A | 6/1997 | McGee et al. | |
| 5,643,197 A | 7/1997 | Brucker et al. | |
| 5,647,869 A | 7/1997 | Goble et al. | |
| 5,656,029 A | 8/1997 | Imran et al. | |
| 5,658,278 A | 8/1997 | Imran et al. | |
| 5,671,747 A | 9/1997 | Connor | |
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | Lafontaine | |
| 5,678,550 A | 10/1997 | Bassen et al. | |
| 5,680,860 A | 10/1997 | Imran | |
| 5,681,278 A | 10/1997 | Igo et al. | |
| 5,681,294 A | 10/1997 | Osborne et al. | |
| 5,681,308 A | 10/1997 | Edwards et al. | |
| 5,687,723 A | 11/1997 | Avitall | |

(56) References Cited

U.S. PATENT DOCUMENTS

| | | | |
|---|---|---|---|
| 5,687,737 | A | 11/1997 | Branham et al. |
| 5,688,267 | A | 11/1997 | Panescu et al. |
| 5,690,611 | A | 11/1997 | Swartz et al. |
| 5,697,536 | A | 12/1997 | Eggers et al. |
| 5,697,882 | A | 12/1997 | Eggers et al. |
| 5,697,925 | A | 12/1997 | Taylor |
| 5,697,927 | A | 12/1997 | Imran et al. |
| 5,697,928 | A | 12/1997 | Walcott et al. |
| 5,713,942 | A | 2/1998 | Stern |
| 5,716,389 | A | 2/1998 | Walinsky et al. |
| 5,718,241 | A | 2/1998 | Ben-Haim et al. |
| 5,718,701 | A | 2/1998 | Shai et al. |
| 5,720,775 | A | 2/1998 | Larnard |
| 5,722,402 | A | 3/1998 | Swanson et al. |
| 5,730,074 | A | 3/1998 | Peter |
| 5,730,127 | A | 3/1998 | Avitall |
| 5,730,704 | A | 3/1998 | Avitall |
| 5,733,280 | A | 3/1998 | Avitall |
| 5,735,280 | A | 4/1998 | Sherman et al. |
| 5,735,290 | A | 4/1998 | Sterman et al. |
| 5,743,903 | A | 4/1998 | Stern et al. |
| 5,746,224 | A | 5/1998 | Edwards et al. |
| 5,755,760 | A | 5/1998 | Maguire et al. |
| 5,769,846 | A | 6/1998 | Edwards et al. |
| 5,782,828 | A | 7/1998 | Chen et al. |
| 5,785,706 | A | 7/1998 | Bednarek |
| 5,788,636 | A | 8/1998 | Curley |
| 5,792,140 | A | 8/1998 | Tu et al. |
| 5,797,905 | A | 8/1998 | Fleischman et al. |
| 5,797,960 | A | 8/1998 | Stevens et al. |
| 5,800,428 | A | 9/1998 | Nelson et al. |
| 5,800,482 | A | 9/1998 | Pomeranz et al. |
| 5,810,764 | A | 9/1998 | Eggers et al. |
| 5,810,802 | A | 9/1998 | Panescu et al. |
| 5,810,806 | A | 9/1998 | Ritchart et al. |
| 5,827,216 | A | 10/1998 | Igo et al. |
| 5,836,947 | A | 11/1998 | Fleischman et al. |
| 5,840,030 | A | 11/1998 | Ferek-Petric et al. |
| 5,843,021 | A | 12/1998 | Edwards et al. |
| 5,843,152 | A | 12/1998 | Tu et al. |
| 5,844,349 | A | 12/1998 | Oakley et al. |
| 5,846,187 | A | 12/1998 | Wells et al. |
| 5,846,191 | A | 12/1998 | Wells et al. |
| 5,849,028 | A | 12/1998 | Chen |
| 5,861,021 | A | 1/1999 | Thome et al. |
| 5,871,523 | A | 2/1999 | Fleischman et al. |
| 5,871,525 | A | 2/1999 | Edwards et al. |
| 5,873,845 | A | 2/1999 | Cline et al. |
| 5,873,855 | A | 2/1999 | Eggers et al. |
| 5,876,399 | A | 3/1999 | Chia et al. |
| 5,879,295 | A | 3/1999 | Li et al. |
| 5,879,296 | A | 3/1999 | Ockuly et al. |
| 5,879,348 | A | 3/1999 | Owens et al. |
| 5,881,732 | A | 3/1999 | Sung et al. |
| 5,882,346 | A | 3/1999 | Pomeranz et al. |
| 5,885,278 | A | 3/1999 | Fleischman |
| 5,891,142 | A | 4/1999 | Eggers et al. |
| 5,893,848 | A | 4/1999 | Negus et al. |
| 5,895,355 | A | 4/1999 | Schaer |
| 5,895,417 | A | 4/1999 | Pomeranz et al. |
| 5,897,553 | A | 4/1999 | Mulier |
| 5,897,554 | A | 4/1999 | Chia et al. |
| 5,899,898 | A | 5/1999 | Arless et al. |
| 5,899,899 | A | 5/1999 | Arless et al. |
| 5,902,289 | A | 5/1999 | Swartz et al. |
| 5,902,300 | A | 5/1999 | Hahnen et al. |
| 5,904,711 | A | 5/1999 | Flom et al. |
| 5,906,580 | A | 5/1999 | Kline-Schoder et al. |
| 5,906,587 | A | 5/1999 | Zimmon |
| 5,906,606 | A | 5/1999 | Chee et al. |
| 5,908,029 | A | 6/1999 | Knudson et al. |
| 5,913,854 | A | 6/1999 | Maguire et al. |
| 5,916,213 | A | 6/1999 | Haissaguerre et al. |
| 5,916,214 | A | 6/1999 | Cosio et al. |
| 5,921,924 | A | 7/1999 | Avitall |
| 5,921,982 | A | 7/1999 | Lesh et al. |
| 5,925,045 | A | 7/1999 | Reimels et al. |
| 5,927,284 | A | 7/1999 | Borst et al. |
| 5,928,191 | A | 7/1999 | Houser et al. |
| 5,931,810 | A | 8/1999 | Grabek |
| 5,931,819 | A * | 8/1999 | Fariabi ................ 604/525 |
| 5,931,848 | A | 8/1999 | Saadat |
| 5,935,123 | A | 8/1999 | Edwards et al. |
| 5,944,715 | A | 8/1999 | Goble et al. |
| 5,954,661 | A | 9/1999 | Greenspon et al. |
| 5,957,919 | A * | 9/1999 | Laufer ................ 606/28 |
| 5,971,980 | A | 10/1999 | Sherman |
| 5,971,983 | A | 10/1999 | Lesh |
| 5,980,516 | A | 11/1999 | Mulier et al. |
| 5,989,248 | A | 11/1999 | Tu et al. |
| 5,993,412 | A | 11/1999 | Deily et al. |
| 5,993,447 | A | 11/1999 | Blewett et al. |
| 6,004,316 | A | 12/1999 | Laufer |
| 6,004,319 | A | 12/1999 | Goble et al. |
| 6,007,499 | A | 12/1999 | Martin et al. |
| 6,010,500 | A | 1/2000 | Sherman et al. |
| 6,012,457 | A | 1/2000 | Lesh |
| 6,015,391 | A | 1/2000 | Rishton et al. |
| 6,016,811 | A | 1/2000 | Knopp et al. |
| 6,018,676 | A | 1/2000 | Davis et al. |
| 6,019,757 | A | 2/2000 | Scheldrup |
| 6,024,733 | A | 2/2000 | Eggers et al. |
| 6,030,381 | A | 2/2000 | Jones et al. |
| 6,036,687 | A | 3/2000 | Laufer et al. |
| 6,036,698 | A | 3/2000 | Fawzi et al. |
| 6,042,556 | A | 3/2000 | Beach et al. |
| 6,048,333 | A | 4/2000 | Lennox et al. |
| 6,056,744 | A | 5/2000 | Edwards |
| 6,056,745 | A | 5/2000 | Panescu et al. |
| 6,056,746 | A | 5/2000 | Goble |
| 6,056,747 | A | 5/2000 | Saadat et al. |
| 6,063,081 | A | 5/2000 | Mulier |
| 6,066,139 | A | 5/2000 | Ryan et al. |
| 6,068,653 | A | 5/2000 | LaFontaine |
| 6,071,279 | A | 6/2000 | Whayne et al. |
| 6,083,237 | A | 7/2000 | Huitema et al. |
| 6,086,585 | A | 7/2000 | Hovda et al. |
| 6,088,894 | A | 7/2000 | Oakley |
| 6,096,037 | A | 8/2000 | Mulier |
| 6,113,592 | A | 9/2000 | Taylor |
| 6,113,596 | A | 9/2000 | Hooven et al. |
| 6,117,101 | A | 9/2000 | Diederich et al. |
| 6,120,496 | A | 9/2000 | Whayne et al. |
| 6,141,576 | A | 10/2000 | Littmann et al. |
| 6,142,993 | A | 11/2000 | Whayne et al. |
| 6,142,994 | A | 11/2000 | Swanson et al. |
| 6,149,620 | A | 11/2000 | Baker et al. |
| 6,152,920 | A | 11/2000 | Thompson et al. |
| 6,161,543 | A | 12/2000 | Cox et al. |
| 6,165,174 | A | 12/2000 | Jacobs et al. |
| 6,190,384 | B1 | 2/2001 | Ouchi |
| 6,193,716 | B1 | 2/2001 | Shannon, Jr. |
| 6,210,406 | B1 | 4/2001 | Webster |
| 6,210,410 | B1 | 4/2001 | Farin et al. |
| 6,210,411 | B1 | 4/2001 | Hofmann et al. |
| 6,212,426 | B1 | 4/2001 | Swanson |
| 6,216,704 | B1 | 4/2001 | Ingle et al. |
| 6,217,528 | B1 | 4/2001 | Koblish et al. |
| 6,217,576 | B1 | 4/2001 | Tu et al. |
| 6,224,592 | B1 | 5/2001 | Eggers et al. |
| 6,231,518 | B1 | 5/2001 | Grabek et al. |
| 6,231,591 | B1 | 5/2001 | Desai |
| 6,235,020 | B1 | 5/2001 | Cheng et al. |
| 6,235,024 | B1 | 5/2001 | Tu |
| 6,237,605 | B1 | 5/2001 | Vaska et al. |
| 6,238,347 | B1 | 5/2001 | Nix et al. |
| 6,238,387 | B1 | 5/2001 | Miller, III |
| 6,238,393 | B1 | 5/2001 | Mulier et al. |
| 6,245,061 | B1 | 6/2001 | Panescu et al. |
| 6,245,064 | B1 | 6/2001 | Lesh et al. |
| 6,245,065 | B1 | 6/2001 | Panescu et al. |
| 6,251,092 | B1 | 6/2001 | Qin et al. |
| 6,251,110 | B1 | 6/2001 | Wampler |
| 6,251,128 | B1 | 6/2001 | Knopp et al. |

(56) References Cited

U.S. PATENT DOCUMENTS

| | | | |
|---|---|---|---|
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,306,133 B1 | 10/2001 | Tu et al. |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,690 B1 * | 10/2002 | Ouchi ............... A61B 10/06 600/121 |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,498 B1 | 2/2003 | Burbank et al. |
| 6,517,536 B2 | 2/2003 | Hooven et al. |
| 6,527,767 B2 | 3/2003 | Wang et al. |
| 6,537,248 B2 | 3/2003 | Mulier |
| 6,558,382 B2 | 5/2003 | Jahns |
| 6,558,385 B1 | 5/2003 | McClurken et al. |
| 5,697,536 C1 | 6/2003 | Eggers et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,623,437 B2 | 9/2003 | Hinchliffe et al. |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,712,775 B2 | 3/2004 | Burbank et al. |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | da Silva |
| 7,156,845 B2 | 1/2007 | Mulier et al. |
| 7,166,106 B2 | 1/2007 | Bartel et al. |
| 7,189,231 B2 | 3/2007 | Clague et al. |
| 7,200,445 B1 | 4/2007 | Dalbec et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,329,267 B2 | 2/2008 | Weber |
| 7,361,175 B2 | 4/2008 | Suslov |
| 7,364,579 B2 | 4/2008 | Mulier et al. |
| 7,412,977 B2 | 8/2008 | Fields et al. |
| 7,537,595 B2 | 5/2009 | McClurken |
| 7,604,635 B2 | 10/2009 | McClurken et al. |
| 7,608,072 B2 | 10/2009 | Swanson |
| 7,628,789 B2 | 12/2009 | Soltesz et al. |
| 7,645,277 B2 | 1/2010 | McClurken et al. |
| 7,651,494 B2 | 1/2010 | McClurken et al. |
| 7,670,338 B2 | 3/2010 | Albrecht et al. |
| 7,691,050 B2 | 4/2010 | Gellman |
| 7,736,361 B2 | 6/2010 | Palanker |
| 7,770,584 B2 | 8/2010 | Danek et al. |
| 7,811,282 B2 | 10/2010 | McClurken |
| 7,815,634 B2 | 10/2010 | McClurken et al. |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |

(56) References Cited

U.S. PATENT DOCUMENTS

| | | |
|---|---|---|
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | McClurken et al. |
| 8,105,323 B2 | 1/2012 | Buysse et al. |
| 8,172,828 B2 | 5/2012 | Chang et al. |
| 8,177,783 B2 | 5/2012 | Davison et al. |
| 8,216,233 B2 | 7/2012 | McClurken |
| 8,323,276 B2 | 12/2012 | Palanker et al. |
| 8,348,946 B2 | 1/2013 | McClurken |
| 8,361,068 B2 | 1/2013 | McClurken |
| 8,388,642 B2 | 3/2013 | Muni et al. |
| 8,414,572 B2 | 4/2013 | Davison et al. |
| 8,475,455 B2 | 7/2013 | McClurken |
| 2002/0049483 A1 | 4/2002 | Knowlton |
| 2002/0062131 A1 | 5/2002 | Gallo, Sr. |
| 2002/0082634 A1 | 6/2002 | Kammerer et al. |
| 2003/0014050 A1 | 1/2003 | Sharkey et al. |
| 2003/0032954 A1 | 2/2003 | Carranza et al. |
| 2003/0045873 A1 | 3/2003 | Hinchliffe |
| 2003/0050635 A1 | 3/2003 | Truckai et al. |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015050 A1 | 1/2004 | Goto et al. |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0097920 A1 | 5/2004 | Desinger |
| 2004/0111136 A1 | 6/2004 | Sharkey et al. |
| 2004/0111137 A1 | 6/2004 | Shankey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2005/0273097 A1 | 12/2005 | Ryan |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0111709 A1 | 5/2006 | Goble et al. |
| 2006/0247617 A1* | 11/2006 | Danek et al. ............ 606/41 |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0208332 A1 | 9/2007 | Mulier et al. |
| 2008/0015563 A1 | 1/2008 | Hoey et al. |
| 2008/0027429 A1* | 1/2008 | Oyatsu ............ 606/45 |
| 2008/0058796 A1 | 3/2008 | O'Brien et al. |
| 2008/0071270 A1 | 3/2008 | Desinger et al. |
| 2008/0103494 A1 | 5/2008 | Rioux |
| 2008/0207028 A1 | 8/2008 | Schutz |
| 2008/0243031 A1 | 10/2008 | Seibel et al. |
| 2008/0262489 A1 | 10/2008 | Steinke |
| 2009/0054805 A1 | 2/2009 | Boyle, Jr. |
| 2009/0182329 A1 | 7/2009 | Dycus |
| 2009/0264879 A1 | 10/2009 | McClurken et al. |
| 2009/0306655 A1 | 12/2009 | Stangenes |
| 2010/0069904 A1 | 3/2010 | Cunningham |
| 2010/0160906 A1 | 6/2010 | Jarrard |
| 2010/0204560 A1 | 8/2010 | Salahieh et al. |
| 2010/0241178 A1 | 9/2010 | Tilson et al. |
| 2010/0274178 A1* | 10/2010 | LePivert ............ 604/21 |
| 2011/0023888 A1 | 2/2011 | Vazales et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0208185 A1 | 8/2011 | Diamant et al. |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0053419 A1 | 3/2012 | Bloom et al. |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0150165 A1 | 6/2012 | Conley et al. |
| 2012/0157989 A1 | 6/2012 | Stone et al. |
| 2012/0184983 A1 | 7/2012 | Chang et al. |
| 2012/0191084 A1 | 7/2012 | Davison et al. |
| 2012/0253343 A1 | 10/2012 | McClurken et al. |

FOREIGN PATENT DOCUMENTS

| | | |
|---|---|---|
| WO | WO 2009/108950 A2 | 9/2009 |
| WO | WO2010/141417 | 12/2010 |

OTHER PUBLICATIONS

Mark A. Gilger, Gastroenterologic Endoscopy in Children: Past, Present, and Future, Current Opinions in Pediatrics 13:429-434, http://sadieo.ucsf.edu/course/o1d/pre-2005/Pedendo.pdf, 2001, 6 pages.

Momem M. Wahidi et al., State of the Art: Interventional Pulmonology, CHEST 131:261-274, http://chestjournal.chestpubs.org/content/131/1/261.full.pdf+html, 2007, 16 pages.

Kieran McManus, Developing a Thoracoscopic Surgical Service, available at http://web.mac.com/kieran.mcmanus/Chapters/General/Developing_VATS_program.html (no date available), last accessed Jun. 10, 2011, 28 pages.

International Search Report and Written Opinion for International Appl. No. PCT/US2011/062442, European Patent Office, The Netherlands, mailed on May 14, 2012, 19 pages.

* cited by examiner

BRONCHOSCOPE-COMPATIBLE CATHETER PROVIDED WITH ELECTROSURGICAL DEVICE

CROSS-REFERENCE TO RELATED APPLICATION

This application claims the benefit of U.S. Provisional Application No. 61/452,073, filed Mar. 11, 2011, the entire disclosure of which is incorporated by reference in its entirety herein.

BACKGROUND

1. Field

The present invention relates to medical devices and, in particular, to catheters provided with electrosurgical devices that can be safely employed as a part of a catheter system that is inserted into a body, for example, catheters having electrosurgical cutting tips that can be safely employed with outer catheters such as bronchoscopes.

2. Background Art

Medicine is providing ever-increasing demands for devices that can navigate narrow passageways to a desired location within a body so that diagnostic and therapeutic procedures can be performed at that location. Currently, elongated medical devices such as catheters can extend into a body from outside via an access point through various connected passageways to a target location. It is sometimes desirable to perform electrosurgical procedures at the target location.

An electrosurgical procedure involves a medical device that uses electrical energy to perform a procedure such as coagulation, dissection, desiccation and cautery. The electrical energy can be provided in either direct current (DC) form or in alternating current (AC) form. However, low frequency electrical energy, including DC, can stimulate muscle and nerves and have potentially undesirable outcomes such as cardiac arrest, if not properly handled. Higher frequency electrical energy, and in particular electrical energy in the radiofrequency (RF) range, may not stimulate muscle or nerves, and therefore may be better suited to core and coagulate tissue.

Modern day elongated medical devices provide the ability for clinicians to navigate to remote and narrow locations within a body. To provide such access, these elongated medical devices must meet a wide variety of requirements such as a desired length and a sufficiently small outer diameter. Further, such a device must also have a sufficiently large inside diameter to permit navigation and delivery of the required functionality to the remote location. In the case of an RF-powered electrosurgical device located at the end of such an elongated medical device, the inside diameter needs to be both sufficiently large to transfer the required energy of the electrosurgical device, as well as provide sufficient diameter consistent with the aspiration requirements of the device. More specifically, sufficient electrical current needs to be delivered to support the RF power level desired at the particular location in the body. For example, an elongated medical device can include an electrosurgical cutting tip for use in a tissue coring procedure. In such an instance, the size of the inner diameter of the elongated medical device should also permit the required aspiration of cored tissue, smoke, blood, and fluid (e.g., bodily fluid) from that location. Further, it is necessary to ensure that the heat generated in the immediate vicinity of the cutting tip be sufficiently isolated from the rest of the elongated medical device so that the elongated medical device does not deteriorate or self-destruct under the resulting thermal conditions.

To guide the electrosurgical device to the target site within a body, the electrosurgical device can be coupled to an elongated delivery device such as an endoscope, for example, a bronchoscope, or other medical device having a lumen, i.e., a catheter. The electrosurgical device can be advanced through the lumen of the elongated delivery device so that the electrosurgical device exits at the target location. However, if the electrosurgical device is energized while within the lumen of the delivery device, the delivery device can be damaged, which can be very costly. To ensure that such damage to the delivery device is not possible, it would be desirable if the electrosurgical device could not be energized until it exits the distal end of the elongated delivery device.

BRIEF SUMMARY

What is needed is a catheter which includes an electrosurgical device and which can be compatible for use with an outer delivery catheter, such as a flexible or rigid bronchoscope or other endoscope, for insertion into a body. The electrosurgical device can be selectively energized via an electrical adaptor connected to an energy source, so that the electrosurgical device is not energized while disposed in the lumen of the outer catheter but becomes energized when the electrosurgical device exits the distal end of the outer catheter. In some embodiments, the catheter can navigate a tortuous pathway within a body in a highly articulable fashion and can be compatible for use with a flexible bronchoscope, for example. In some embodiments, the catheter can aspirate, core, and/or allow passage of various alternative tools to a target location in the body. In some embodiments, the catheter can be a coring catheter in which the electrosurgical device is an electrosurgical cutting tip for removing tissue cores at the target location. In some embodiments, the cutting tip can include sufficient thermal isolation to permit operation without deterioration or self-destruction of the distal portion of the catheter. The coring catheter can be used with a flexible or rigid bronchoscope equipped with a vision component, and the result is a coring catheter system with articulation, vision, and the ability to core bronchial tumors.

In some embodiments, a catheter system includes an electrical adapter and a catheter. The adaptor includes a hollow adapter body having a longitudinally extending channel and an electrical terminal positioned within the channel. The electrical adapter is configured to be electrically connected to an energy source. The catheter has an elongated body and an electrical connector coupled to a proximal end portion of the elongated body. The electrical connector forms an outer periphery of the catheter along a portion of the longitudinal length of the catheter. The electrical connector is configured to be inserted in the channel of the hollow adapter body. The electrical terminal and the electrical connector are configured to be electrically connected to each other when the electrical connector is advanced to an electrical contact position within the channel, and are configured to be electrically isolated from each other when the electrical connector is proximal of the electrical contact position.

In some embodiments, an electrical adapter includes a hollow body with a first opening at a proximal end portion and a second opening at a distal end portion, the hollow body defining a longitudinally extending channel that extends from the first opening to the second opening. The channel is configured to removably receive a proximal end portion of a catheter having an electrical connector. The distal end portion of the electrical adapter can be configured to connect to a second catheter such that the second opening communicates with a port of the second catheter. An electrical terminal has an exposed, electrically conductive surface positioned within the channel that is configured to selectively contact the electrical connector of the catheter. A plug terminal is electrically connected to the electrical terminal and is configured to be selectively, electrically connected to an energy source.

In some embodiments, a catheter includes an elongated body, an electrical connector coupled to a proximal end of the elongated body, and a tool coupled to the distal end portion of the elongated body, the tool being electrically connected to the electrical connector. The electrical connector forms an outer periphery of the catheter along a portion of a longitudinal length of the catheter and has an electrically conductive surface. The electrical connector is configured to be removably disposed in a channel of an electrical adapter that is coupled to a lumen of a second catheter and that is connected to an energy source. The conductive surface of the electrical connector selectively contacts a conductive surface of an electrical terminal in the channel for selectively, electrically connecting the energy source to the electrical connector.

Methods for using a catheter system to treat tissue according to embodiments described herein are also provided.

BRIEF DESCRIPTION OF THE DRAWINGS/FIGURES

Embodiments of the present invention are described with reference to the accompanying drawings. In the drawings, like reference numbers indicate identical or functionally similar elements.

The features and advantages of the present invention will become more apparent from the detailed description set forth below when taken in conjunction with the drawings, in which like reference characters identify corresponding elements throughout.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such a feature, structure, or characteristic in connection with other embodiments whether or not explicitly described.

Figure 1:
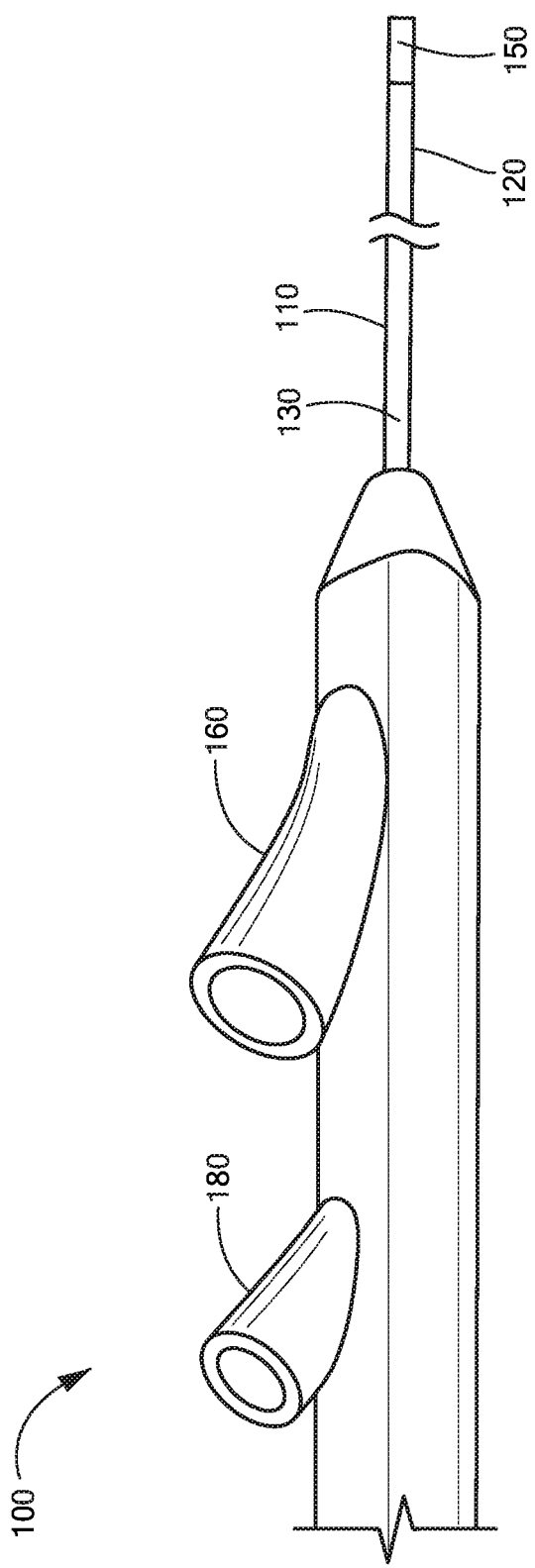
FIG. 1 illustrates a side view of an outer catheter to which an inner catheter can be coupled, according to an embodiment presented herein.
Figure 9:
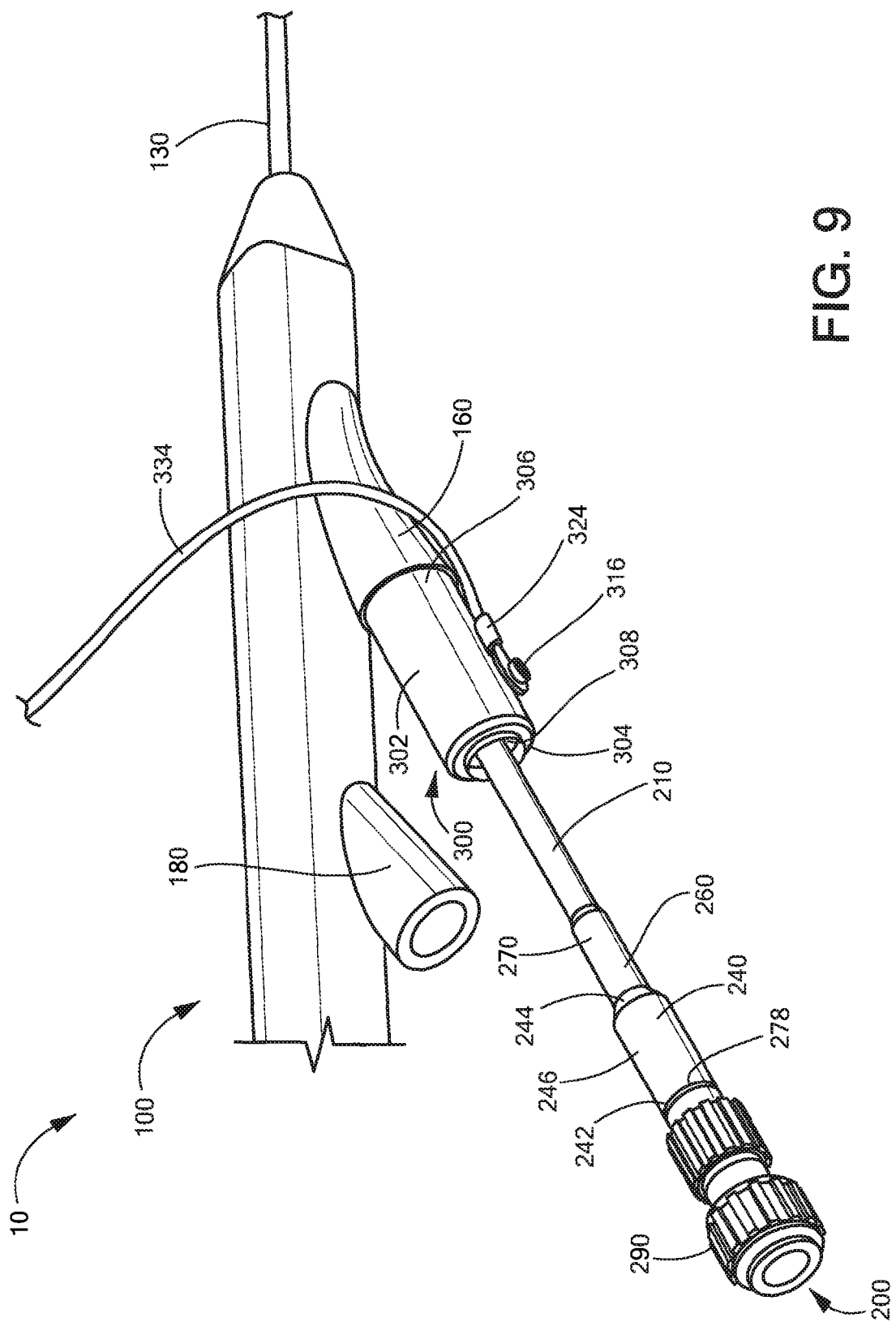
FIG. 9 illustrates a perspective view of a catheter system with the inner catheter partially inserted, according to an embodiment presented herein.

In some embodiments, a catheter system can include an outer catheter, an inner catheter coupled to the outer catheter, and an electrical adapter that can selectively connect the inner catheter to an energy source. FIG. 1 depicts an embodiment of an outer catheter 100 to which an inner catheter (such as later-described catheter 200) can be coupled (see FIGS. 9 and 10). In exemplary embodiments, outer catheter 100 is a flexible catheter and can be coupled to multiple flexible, inner catheters. In some embodiments, outer catheter 100 is an endoscope (for example, a flexible or rigid bronchoscope), or other medical device. Outer catheter 100 contains an elongated body 110 having a distal end portion 120 with a distal tip 150 and a proximal end portion 130. Based on the location within the body for which access is sought, elongated body 110 can take on a wide variety of lengths. Outer catheter 100 can have one or more ports, for example, ports 160 and 180, that provide access to one or more lumens of outer catheter 100 to permit passage of other catheters or instruments (e.g., inner catheters, wires to provide power to inner catheters, a vision system (e.g., fiber-optic device), an aspiration needle, a drug-delivery catheter, a biopsy instrument, a cutter, a balloon catheter, a electrocautery instrument, a hemostatic sealing instrument, etcetera).

Elongated body 110 can be articulable and flexible such that the elongated body 110 can be navigated through a particular tortuous passageway. The degree of articulation and flexibility is dependent upon a desired pathway's particular twists and bends, and the curvature thereof. Tighter twists and bends demand greater flexibility than more gentle twists or bends. Accordingly, the flexibility for embodiments of catheter 100 is application dependent. A bronchoscope embodiment of the present invention can navigate as deep in a bodily passageway as the bronchoscope is able to be delivered, for example, to trachea in some embodiments, to the primary bronchi in some embodiments, to the lobar in some embodiments, to the segmentals in some embodiments, and to the subsegmentals in some embodiments. For example, in some embodiments, a bronchoscope embodiment of the present invention can require greater flexibility to navigate to the 5th branch of an adult bronchi system than would be required for a catheter to navigate a more modest pathway in the body.

Access by catheter 100 within the body can be by any natural orifice, small incision or through the use of any minimally invasive surgery in order to perform the desired task. Such access points include but are not limited to mouth, nose, urethra, and radial, jugular and femoral arteries. Lengths of catheter 100 (to which various inner catheters can be coupled) can range from 1 cm (as would be applicable in certain brain procedures), to a 5 cm length bronchoscope for use in a procedure on a small infant, to lengths in excess of 130 cm for use in various scopes such as endoscopes and bronchoscopes for adult procedures. In exemplary embodiments as a flexible bronchoscope, elongated body 110 would be from about 62.5 cm to about 125 cm (25 to 50 inches) long, with an outer diameter from about 4.0 to about 4.5 mm and an inner diameter from about 2.5 to about 3.0 mm.

Figure 2A:
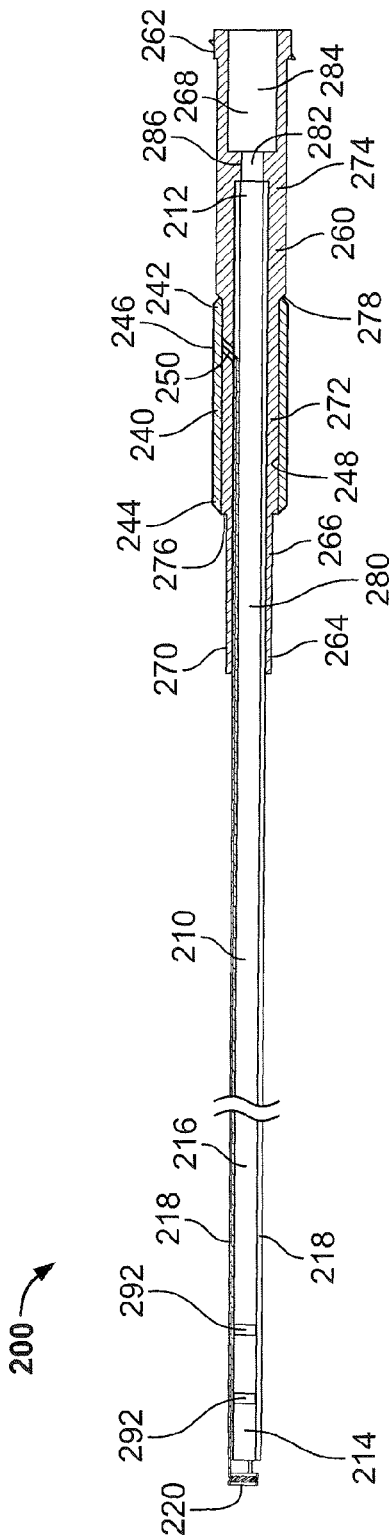
FIG. 2A illustrates a longitudinal cross-sectional view of an inner catheter according to an embodiment presented herein.
Figure 2B:
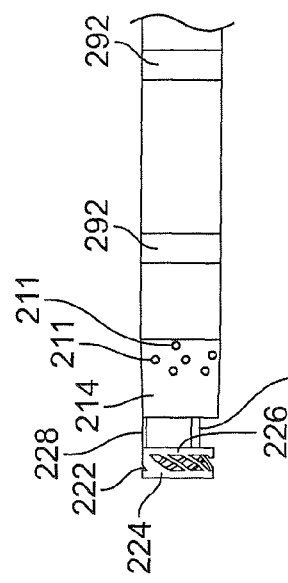
FIG. 2B illustrates an enlarged view of a distal end portion of the inner catheter of FIG. 2A to which is coupled an electrosurgical cutting tip, according to an embodiment presented herein.
Figure 2C:
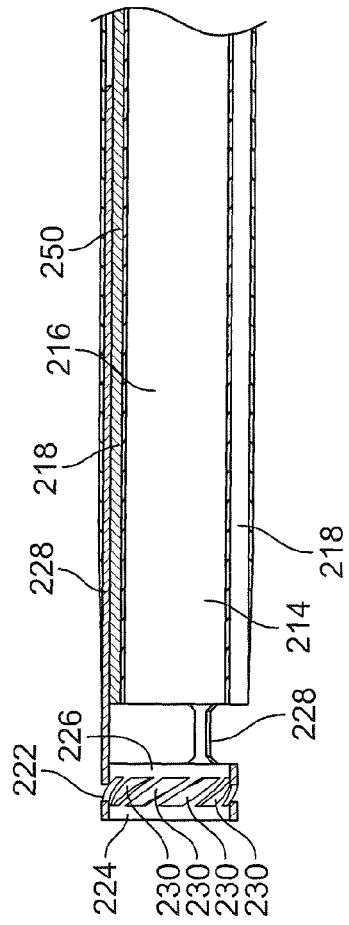
FIG. 2C illustrates an enlarged longitudinal cross-sectional view of the distal end portion of the inner catheter of FIG. 2B, according to an embodiment presented herein.

FIGS. 2A-2C illustrate an inner catheter 200 which can be coupled to outer catheter 100, according to some embodiments presented herein. As shown, catheter 200 can include an elongated body 210 having a proximal end portion 212 and a distal end portion 214. Elongated body 210 can be articulable and flexible such that the elongated body 210 can be navigated, either independent or dependent of outer catheter 100, through a particular tortuous passageway. As discussed above, the degree of articulation and flexibility is dependent upon a desired pathway's particular twists and bends, and the curvature thereof. Accordingly, the flexibility for embodiments of elongated body 210 is application dependent. For example, a catheter 200 that is being coupled with a bronchoscope can require greater flexibility than would be required for catheter 200 being coupled to a catheter 100 being used to navigate a more modest pathway in the body.

Elongated bodies 210 can be provided with one or more lumens that can serve as a passageway for one or more navigation wires (e.g., a tether) that provides a mechanism for articulation of inner catheter 200 and can serve as a mechanism for articulation of a catheter system including inner catheter 200 and outer catheter 100 (in addition to any articulation mechanism provided by outer catheter 100. For example, as shown in later-described FIG. 6A, elongated body 210 can include one or more lumens (see FIG. 6A) which can serve as a passageway for one or more navigation wires that allow for articulation of elongated body 210 of inner catheter 200, and allow steerability of the inner catheter 200 through the tortuous passageways and around contours.

As described herein, flexibility of elongated bodies 110 and 210 can be controlled by the dimensions of elongated bodies 110 and 210, the durometers of the materials used in their construction, and on the dimensions, materials and construction of elongated bodies 110 and 210. Elongated bodies 110 and 210 can be made of any suitable material that provides an appropriate compromise between strength, flexibility, and other requirements. For example, polymers with high hardness or durometer can meet the longitudinal strength or stiffness requirements, while materials with low hardness or durometer can meet the flexibility requirements. For example, suitable materials that can provide the appropriate compromise between these two extremes include silicones, polyurethane, elastomeric polyamides, block polyamide (such as Pebax®, a polyether block amide, available from Arkema, Colombes, France), Tecoflex® and various co-polymers. The range of durometers suitable for the manufacture of elongated bodies 110 and 210 include durometers in the range 20 to 70 Shore A. In some embodiments, the distal end portion 214 of elongated body 210 can be formed from one or more coaxial segments coupled together, in which each segment is made of a material of a particular durometer with its adjacent segment having a different durometer. Manipulation of the navigation wire(s) disposed in the lumen(s) of catheter body 210 can also be used to control deflection of the segmented distal end portion of the inner catheter during a surgical procedure at a target location to create unique configurations of the articulated distal end portion 214. Exemplary inner and outer catheters that can be employed as outer catheter 100 and inner catheter 200 are described in U.S. patent application Ser. No. 12/862,677, filed Aug. 24, 2010, and entitled "Highly Articulable Catheter," which is incorporated herein by reference in its entirety for all purposes.

Figure 3A:
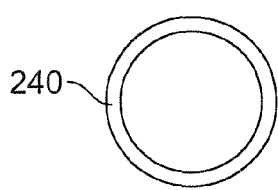
FIG. 3A illustrates an axial view of an electrical connector according to an embodiment presented herein.
Figure 3B:
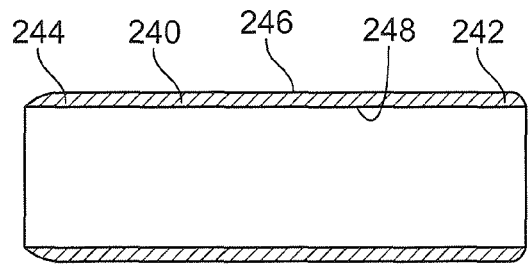
FIG. 3B illustrates a longitudinal cross-sectional view of an electrical connector according to an embodiment presented herein.
Figure 4A:
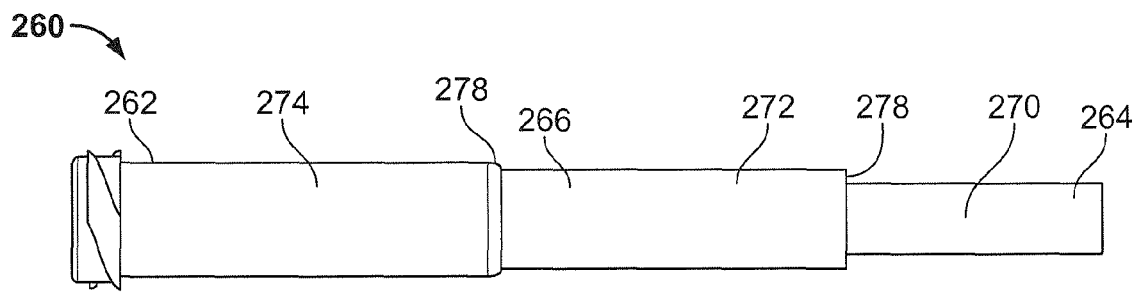
FIG. 4A illustrates a side view of a fitting of the inner catheter of FIG. 2A, according to an embodiment presented herein.
Figure 4B:
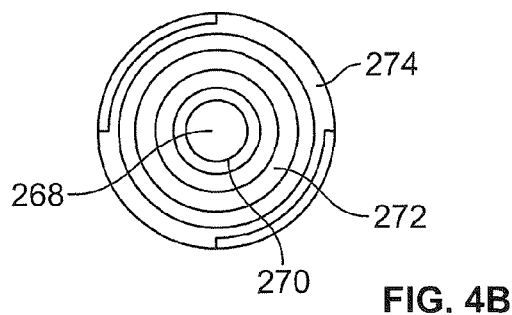
FIG. 4B illustrate an axial view of the fitting of FIG. 4A according to an embodiment presented herein.
Figure 4C:
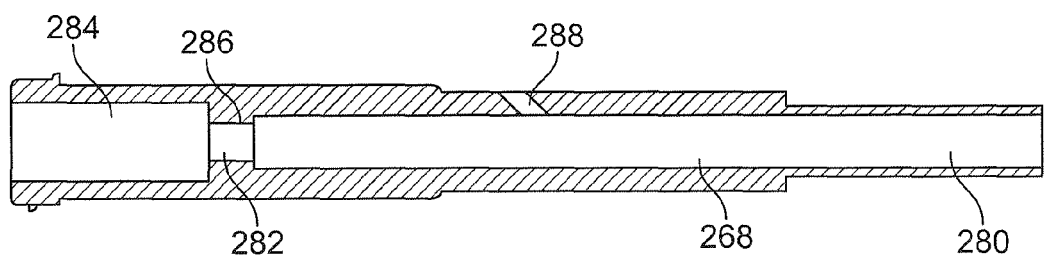
FIG. 4C illustrates a longitudinal cross-section view of the fitting of FIG. 4A according to an embodiment presented herein.
Figure 5:
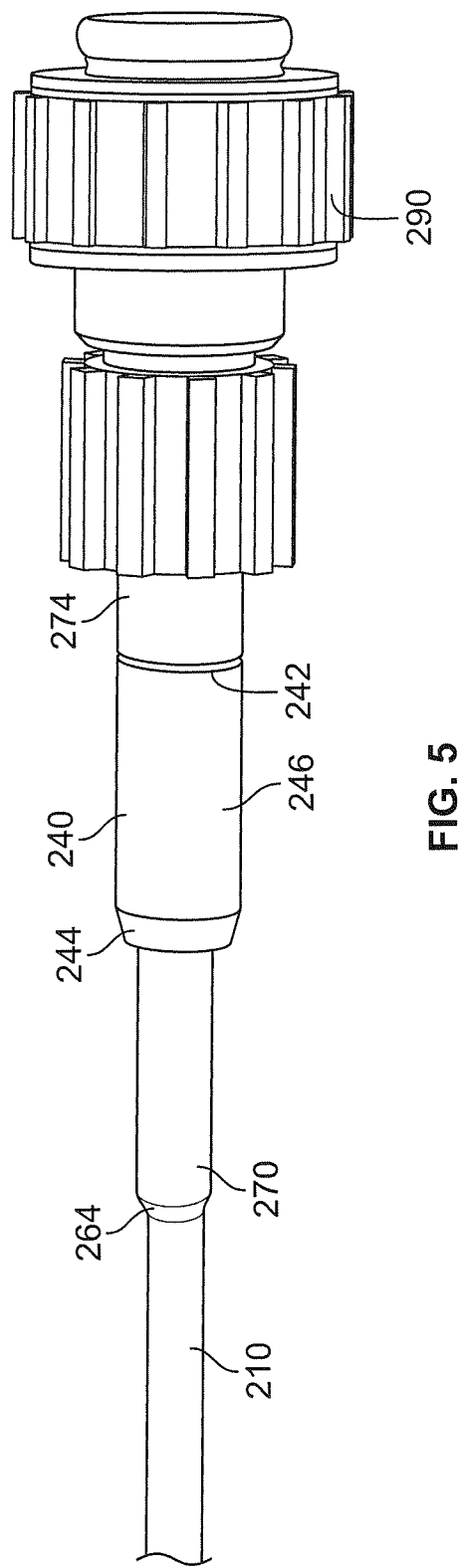
FIG. 5 illustrates a side view of a proximal end portion of the inner catheter of FIG. 2A, showing an elongated body, the fitting, the electrical connector, and a handle according to an embodiment presented herein.

Catheter 200 can also include an electrical connector 240 coupled to proximal end portion 212 of elongated body 210. In an embodiment, as illustrated in FIGS. 2A, 3A, 3B, and 5, electrical connector 240 can be a hollow cylinder defining a longitudinal channel extending from a proximal end portion 242 to a distal end portion 244 of electrical connector 240. The hollow cylinder of electrical connector 240 can have an outer surface 246 and an inner surface 248. In an embodiment, the edges of proximal end portion 242 and distal end portion 244 can be tapered as seen in FIGS. 3B and 5.

In some embodiments, electrical connector 240 is coupled to elongated body 210 by using a fitting 260. As illustrated in FIGS. 2A, 4A-4C, and 5, fitting 260 can have a hollow body 266 defining a longitudinal channel 268. Hollow body 266 can have a proximal end portion 262 and a distal end portion 264. Hollow body 266 can be generally cylindrical. For example, hollow body 266 can include a cylindrical distal portion 270, a cylindrical middle portion 272, and a cylindrical proximal portion 274, each having a larger diameter than the adjacent, distal portion. A step or shoulder 276 can be formed between distal portion 270 and middle portion 272, and a step or shoulder 278 can be formed between middle portion 272 and proximal portion 274. In some examples, the outer diameter of middle portion 272 corresponds to the inner diameter of the channel defined by electrical connector 240. For example, when fitting 260 is inserted into electrical connector 240, a snug fit occurs between a portion, for example, middle portion 272, of electrical connector 240. Electrical connector 240 can contact shoulder 278. Accordingly, electrical connector 240 forms an outermost periphery along a portion of the longitudinal length of catheter 200.

In some embodiments, channel 268 can have a distal portion 280, a middle portion 282, and a proximal portion 284 of one or more different diameters. For example, the inner diameter of middle portion 282 can be less than the inner diameter of either the distal portion 280 or the proximal portion 284, creating a shoulder 286 there between. In some embodiments, the inner diameter of distal portion 280 is sized to closely receive proximal end portion 212 of elongated body 210. In another embodiment, when proximal end portion 212 of elongated body 210 is fully inserted into distal portion 280 of fitting 260, the edge of proximal end portion 212 contacts shoulder 286.

In exemplary embodiments, fitting 260 can also have a radial opening 288 extending from channel 268 to an outer surface of fitting 260. For example, opening 288 can extend through the wall of middle portion 272 at a 45 degree angle. Opening 288 can be used as conduit for a wire 250 that contacts inner surface 248 of electrical connector 240.

In some embodiments, fitting 260 can be coupled to a leur system 290 configured for use with various diagnostic or therapeutic procedures. For example, as illustrated in FIG. 5, fitting 260 can be coupled to a hemostasis valve system 290. The hemostasis valve system 290 can include, for example, a Tuohy-Borst adapter. For example, the Tuohy-Borst adapter can be a FLO 30™ Tuohy-Borst Adapter manufactured by Qosina Corp. of Edgewood, N.Y. In some examples, the adapter of system 290 can define a channel having an inner diameter that closely corresponds to the outer diameter of proximal portion 274 of fitting 260.

Figure 6A:
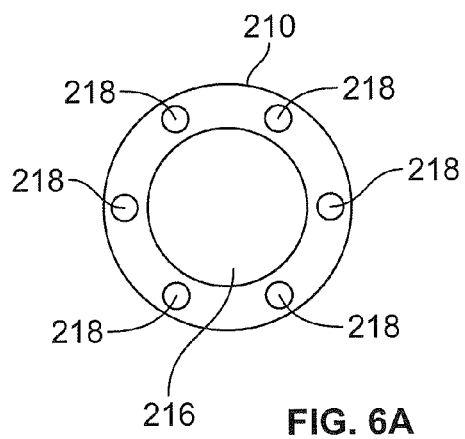
FIG. 6A illustrates an axial view of the elongated body of the inner catheter of FIG. 2A according to an embodiment presented herein.
Figure 6B:
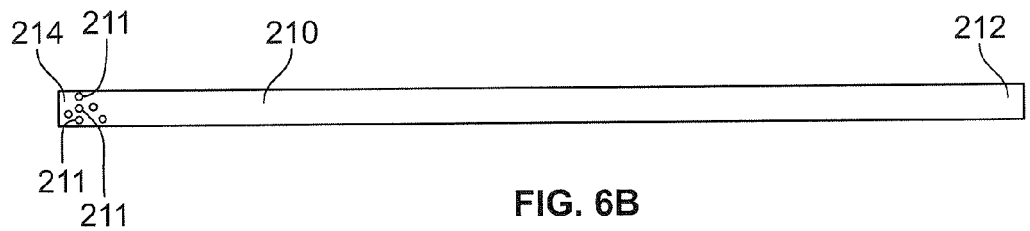
FIG. 6B illustrates a side view of the elongated body of the inner of FIG. 2A according to an embodiment presented herein.

Elongated body 210 can have a lumen extending from proximal end portion 212 to distal end portion 214. In another example, elongated body 210 can have two or more lumens. For example, as illustrated in FIG. 6A, elongated body 210 can have a central lumen 216 surrounded by seven periphery lumens 218. In various embodiments, one or more lumens can be used for articulation, for example, by carrying a navigation wire (e.g., a tether); for a conduit of a conductor, for example, wire 250; for delivery or securing a tool 220 (such as a diagnostic or therapeutic tool); or for aspiration. For example, in some embodiments, one or more aspiration holes 211 are provided on the sidewall of body 210 at distal end portion 214 (see FIGS. 2B and 6B). In some embodiments, multiple aspiration holes 211 are provided on the sidewall. Holes 211 can be provided in any relational configuration, for example, holes 211 can be circumferentially disposed on the body sidewall, and/or longitudinally disposed on the body with respect to each other. Each aspiration hole 211 can fluidly connect to one or more lumens 218, and can be used to aspirate, for example, cored tissue, smoke, blood, and fluid (e.g., bodily fluid).

FIG. 6A illustrates the lumen configuration as being symmetric and concentric. In some embodiments, elongated body 210 can have asymmetric and eccentric lumen configurations. Particularly, lumens 216 and 218 can be of different physical dimensions and placed in a variety of different physical locations consistent with being located within elongated body 210. In some embodiments, the outer diameter of elongated body can be from about 2.5 to about 3.5 mm, and the inner diameter of central lumen 216 can be from about 2.0 to about 2.5 mm.

In various embodiments, catheter 200 can have a variety of tools 220, such as diagnostic and therapeutic tools that can be used to perform various procedures at a desired location within the body of a living organism such as a human or animal, coupled to distal end portion 214. Diagnostic tools can include, for example, assorted biopsy tools and devices, and therapeutic tools include, for example, advanced-energy and pharmaceutical tools. Based on the location within the body for which access is sought, elongated body 210 can take on a wide variety of lengths.

In some embodiments, tool 220 can be an electrically-powered device, including for example, a laser, an argon beam, cutting tip, wire snare, a monopolar or bipolar device, an ultrasonic device, or other electrosurgical device that is coupled to a corresponding energy source. In some embodiments, tool 220 can be an electrosurgical device that can be used in a variety of procedures in pulmonology, cardiology, urology, gastroenterology, neurology, or any other procedure involving a body lumen or cavity. For example, tool 220 can be an electrosurgical cutting tip that is electrically connected to an RF energy source such as electrosurgical cutting tip 220 illustrated in the embodiments of FIGS. 2A-2C and 7A-7C. Exemplary electrosurgical cutting devices that can be employed as electrosurgical cutting tip 220 are described in U.S. patent application Ser. No. 12/912,659, filed Oct. 26, 2010, and entitled "Electrosurgical Cutting Devices," which is incorporated herein by reference in its entirety for all purposes. In some embodiments, tool 220 can be connected to an ultrasonic energy source, and the tool 220 can be a piezoelectric cutting tip made of, for example, lead magnesium niobate.

In some embodiments, electrosurgical cutting tip 220 can include a cutting portion 222 having a distal end portion 224 and a proximal end portion 226. In some embodiments, cutting portion 222 can have a substantially cylindrical or annular shape (e.g., ring-shaped) with distal end portion 224 defining a cutting edge.

Cutting portion 222 can have one or more struts 228 extending proximally from proximal end portion 226. Struts 228 can provide mechanical support to couple tool 220 to distal end portion 214 of elongated body 210, and can provide electrical connectivity to cutting portion 222. Struts 228 can also space cutting portion 222 away from distal end portion 214 of elongated body 210, creating a gap there between. The gap between cutting portion 222 and distal end portion 214 provides a thermal barrier to reduce heat transfer from cutting portion 222 to elongated body 210. Additionally, struts 228 can provide an open interior space that allows cored tissue to be aspirated and removed from the target location via a lumen in elongated catheter.

In exemplary embodiments, cutting portion 222 has an outer diameter of about 2.0 to about 3.5 mm, a length (in the longitudinal direction of catheter 200) of about 0.5 to about 1.9 mm, a wall thickness of about 0.08 to about 0.5 mm, and is separated from elongated body 210 by a gap of about 0.25 to about 1.9 mm. These dimensions are merely exemplary and can be larger or smaller depending on the application.

In some embodiments, electrosurgical cutting tip 220 can have three struts 228 that are used to couple electrosurgical cutting tip 220 to distal end portion 214 of elongated body 210. Struts 228 are positioned so as to ensure sufficient mechanical stability in all three degrees of freedom for cutting portion 222. Struts 228 extend into lumens, for example, periphery lumens 218, of elongated body 210 and are mechanically secured therein. In some embodiments, struts 228 can have one or more barbs 232. Barbs 232 project from a surface of struts 228. Each barb 232 can have a width that is slightly larger than a diameter of a lumen, for example, periphery lumen 218, in which each strut 228 is disposed. Accordingly, when each strut 228 is inserted into a lumen, the barbs 232 project into the surface defining the lumen, securing each strut 228 to elongated member 210. In exemplary embodiments, struts 228 can be from about 11.0 to about 13.0 mm in length, and thus the majority of the length of struts 228 is secured within the lumens of elongated body 210. However, the length can be longer or shorter depending on the application.

In some embodiments, at least one of strut 228 is connected (via welding or any other suitable method of securing) to a wire 250 within a lumen in elongated body 210. Wire 250 can run the length of elongated body 210 and through opening 288 in fitting 260 to connect to electrical connector 240. Accordingly, electrosurgical cutting tip 220 can be connected to an energy source via electrical adapter 300. An exemplary energy source is a Force FX™ RF electrosurgical generator that is manufactured by Valleylab, a division of Tyco Healthcare Group located in Boulder, Colo. With such an electrical connection, cutting portion 222 can be energized with, for example, RF energy. Cutting portion 222 and struts 228 can be made of any suitable conductive, biocompatible material that provides the required mechanical strength and current carrying ability as well as provides a suitable cutting edge at distal end portion 224. The material should also handle the heat generated during an electrosurgical procedure. For example, tool 220 can be made of stainless steel, gold, or platinum.

In some embodiments, electrosurgical cutting tip 220 can be a monopolar device such that a return pad is required to be positioned on the body at a suitable location. Thus, electrical current such as RF current is emitted from cutting portion 222 into the tissue immediately surrounding cutting portion 222. From this tissue, the RF current propagates towards the return pad at which point the RF current converges at the return pad and exits the body. Alternatively, electrosurgical cutting tip 220 can be a bipolar device, and in some embodiments, a lumen of inner catheter 200 can be used as a passageway for supplying non-conductive or conductive fluid (e.g., saline) to tip 220. In additional embodiments, electrosurgical cutting tip 220 can be selectively switched between monopolar and bipolar modes.

In some embodiments of an electrosurgical cutting tip 220, separation of tissue can be achieved by applying pressure in the distal direction while delivering energy to the tip 220, for example, RF energy. Upon separation of the tissue of interest, aspiration of the separated tissue proceeds by way of the interior of the sections of cutting portion 222 and the interior of its attached elongated body 210. Cutting portion 222 is particularly appropriate for longer portions of tissue removal that require tunneling forward over an extended length, with separation and aspiration as one moves forward. For example, central lumen 216 and aspiration hole(s) 211 (see FIGS. 6A and 6B) can be used to aspirate cored tissue, smoke, blood, and fluid (e.g., bodily fluid). In some embodiments, cutting portion 222 of cutting tip 220 can be navigated by articulating distal end portion 214, for example, by using navigation wires disposed in one or more periphery lumens 218.

With respect to the thermal environment, significant heat can be dissipated locally in the immediate vicinity of cutting portion 222. Particularly vulnerable to the temperature increases is distal end portion 214 of elongated body 210. To provide sufficient electrical energy to cutting portion 222 without damaging the cutting portion 222, thermal considerations should be accommodated. In an embodiment of cutting portion 222, a gap (see FIGS. 2A-2C) is provided between cutting portion 222 and elongated body 210 to which cutting portion 222 is attached. The gap provides additional thermal resistance, and therefore, heat transfer towards elongated body 210 is reduced, protecting the stability and integrity of elongated body 210.

Figure 7A:
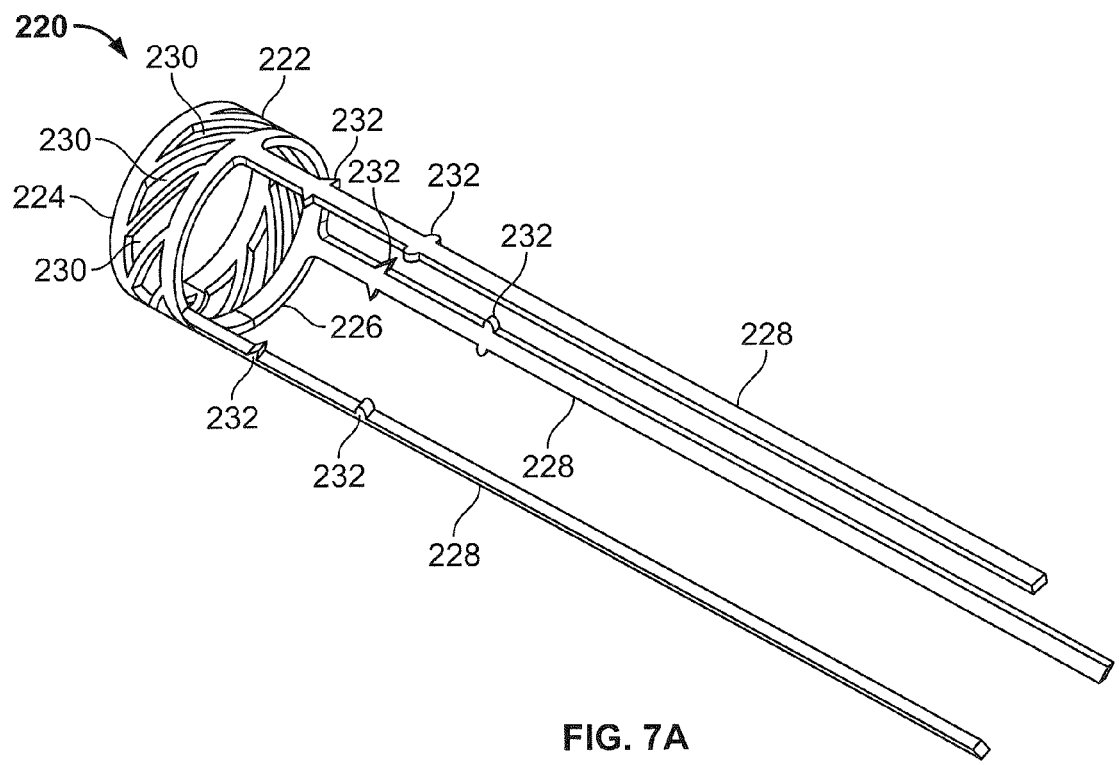
FIG. 7A illustrates a perspective view of the cutting tip shown in FIG. 2B according to an embodiment presented herein.
Figure 7B:
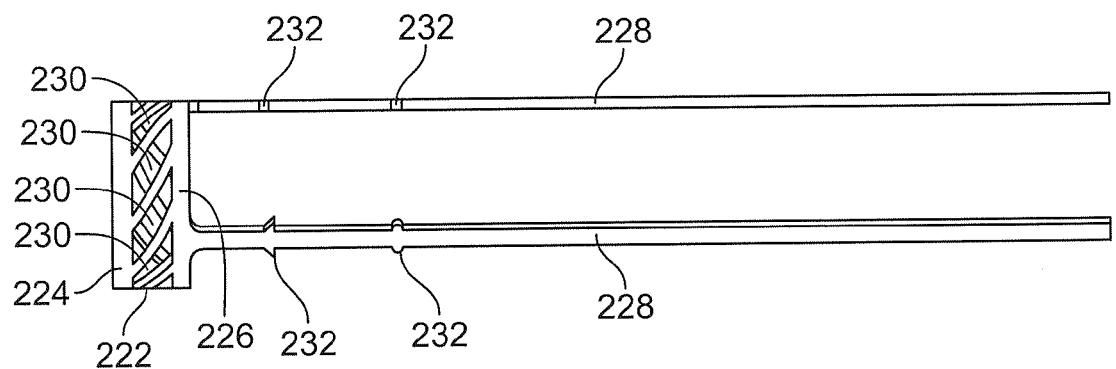
FIG. 7B illustrates a side view of the cutting tip of FIG. 7A according to an embodiment presented herein.
Figure 7C:
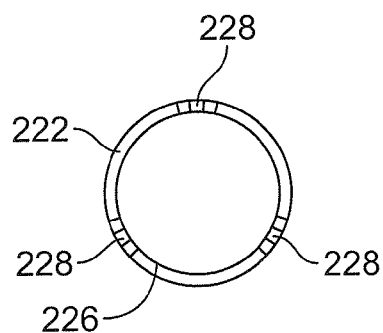
FIG. 7C illustrates an axial view of the cutting tip of FIG. 7A according to an embodiment presented herein.

In some embodiments, as shown in FIGS. 2A-2C, 7A, and 7B, thermal resistance can be increased by using one or more openings or slots 230 in cutting portion 222. For example, as illustrated in FIGS. 7A-7C, cutting portion 222 can have slots 230 that reduce the amount of thermally conducting material in the thermal pathway between distal end portion 224 and proximal end portion 226 of cutting portion 222. Slots 230 decrease heat transfer from the heat source, for example, the cutting edge defined by distal end portion 224, to elongated body 210 via struts 228. Instead of a thermal path that consists of a solid ring, portions of cutting portion 222 have been removed to form slots 230, which thereby increases the thermal resistance. As known by one of ordinary skill in the relevant arts, increased thermal resistance diminishes the ability for heat to propagate to elongated body 210, increased temperature effects are confined to the cutting edge at distal end portion 224, and distal end portion 214 of elongated body 210 is thereby protected from thermal damage. In one example, cutting portion 222 can have a plurality of rectangular slots 230 having a width from about 0.10 to about 0.80 mm and a length of about 0.10 to 0.80 mm. The number of slots 230 and the dimensions of slots 230 can take on a wide range consistent with maintaining the structural integrity of substantially cutting portion 222 while providing an appropriate thermal resistance.

In some embodiments, slots 230 can be slanted or angled relative to the longitudinal axis of catheter 200, as illustrated in FIGS. 2A-2C and 7A-7C. By angling slots 230, the length of the thermal path between the source of the heat at distal end portion 224 of cutting portion 222 and distal end portion 214 of elongated body 210 via struts 228 is increased, which increases the thermal resistance. Thus, for the same length of slot, slanted slots 230 lengthen the thermal path and thereby increase the thermal resistance relative to slots that run along the longitudinal axis. In exemplary embodiments, slots 230 are angled at about 25 to 50 degrees from the longitudinal axis. The slant angle, however, can take on a wide range of angles consistent with maintaining the structural integrity of cutting portion 222 while providing an appropriate thermal resistance.

In some embodiments, distal end portion 214 of elongated body 210 can have position indicators 292 configured to be seen with imaging technologies such as fluoroscopy and ultrasound.

FIGS. 8A-8D illustrate an electrical adapter 300 according to some embodiments. Electrical adapter 300 is electrically connected to an energy source, and can selectively connect electrical connector 240 of catheter 200 (and therefore tool 220) to the energy source. In this embodiment, electrical adapter 300 includes a hollow body 302 having a proximal end portion 304 and a distal end portion 306. Hollow body 302 can define a longitudinal channel 308 that extends from proximal end portion 304 to distal end portion 306. Channel 308 is configured to receive catheter 200. The inner diameter of channel 308 is sized to allow elongated body 210 of catheter 200 to pass therethrough, yet closely receive electrical connector 340 coupled to proximal end portion 212 of elongated body 210. To create a seal, one or more O-rings 330 can be positioned in channel 308 to engage electrical connector 240 of catheter 200 when inserted. A proximal portion 310 of channel 308 can be tapered to help align catheter 200 when inserted through channel 308. Distal end portion 306 of body 302 is configured to couple to a port of catheter 100, for example port 160, such that a distal portion 312 of channel 308 is connected to a lumen in catheter 100. For example, distal end portion 306 of body 302 can include a plurality of detent tabs 332 that correspond to a plurality of detent receptacles surrounding port 160.

Figure 8A:
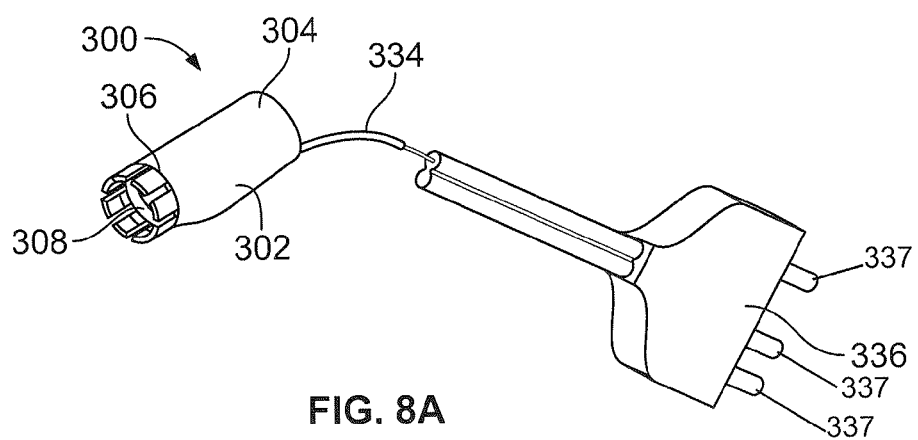
FIG. 8A illustrates a perspective view of an electrical adapter according to an embodiment presented herein.
Figure 8B:
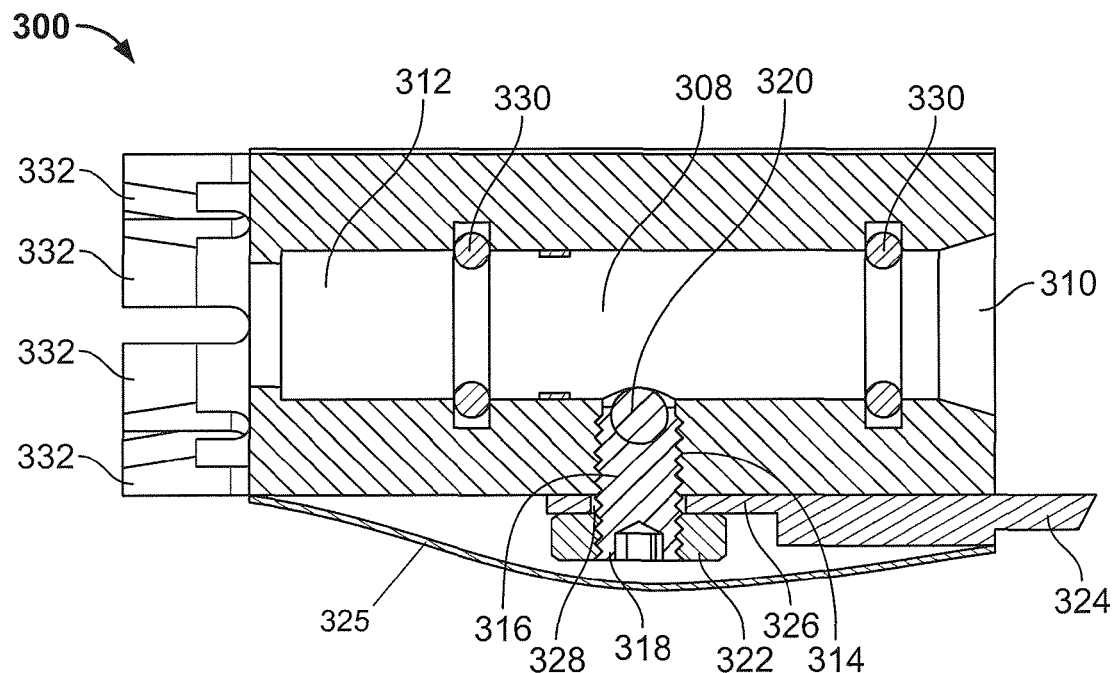
FIG. 8B illustrates a longitudinal cross-sectional view of a body of the electrical adapter of FIG. 8A, showing an electrical terminal, according to an embodiment presented herein.
Figure 8C:
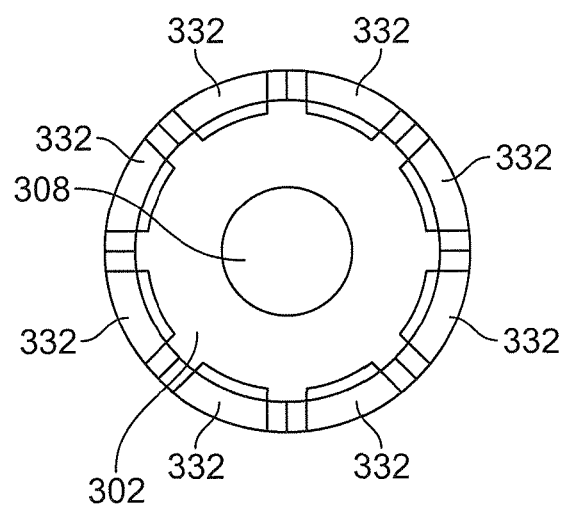
FIG. 8C illustrates an axial view of the body of the electrical adapter of FIG. 8A according to an embodiment presented herein.
Figure 8D:
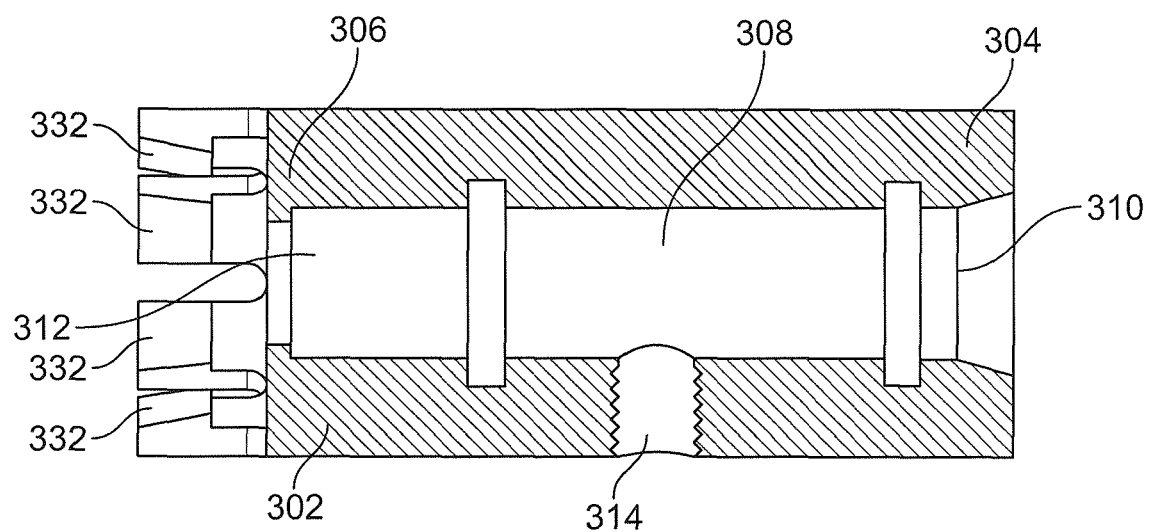
FIG. 8D illustrates a longitudinal cross-sectional view of the body of the electrical adapter of FIG. 8A without the electrical terminal, according to an embodiment presented herein.

Electrical adapter 300 can also have an electrical terminal 316 positioned within channel 308 for electrically coupling the energy source to electrical connector 340. In some embodiments, electrical adaptor 300 can employ any configuration known in the art for selectively electrically coupling electrical components together. For example, in some embodiments, electrical terminal 316 can include a suitable electrical switch which can be actuated when terminal 316 becomes coupled with electrical connector 340 so as to deliver energy from the energy source to electrical connector 340. In some embodiments, electrical terminal 316 can be an electrically conductive surface that is exposed in channel 308. In some embodiments, the electrically conductive surface can be biased towards the center of channel 308. For example, as illustrated in FIG. 8B, the electrically conductive surface can be a ball bearing 320 that is biased by a spring force towards the center of channel 308. Ball bearing 320 can be housed in a set screw 318 that passes through an opening 314 defined in the wall of adapter body 302. In some embodiments, the electrically conductive surface can be a leaf spring or any other suitable device having a conductive surface biased towards the center of channel 308. In some embodiments (not shown), the spring-biased electrically conductive surface can instead be provided on electrical connector 340, which can engage a conductive surface provided in channel 308.

Electrical terminal 316 is coupled to the energy source on one end of electrical terminal 316, for example, via a wire 334 and an energy source connector 336 (e.g., a plug). Energy source connector 336 can be configured to couple with any suitable energy source. For example, as illustrated in FIG. 8A, energy source connector 336 can be a plug having one or more terminals 337 (e.g., prongs) having conductive surfaces. In the embodiment of FIG. 8A, plug 336 has three prongs 337 which can be plugged into a suitable power generator for electrically connecting the generator to electrical terminal 316. As an example, the three prong plug connector may be configured to provide monopolar power from a suitable power generator to electrical terminal 316, for ultimately supplying monopolar power to a monopolar tip (which can be tool 220) as further discussed below.

As illustrated in FIGS. 8A and 8B, set screw 318 and ball bearing 320 can be connected to the energy source via wire 334 and energy source connector 336. Wire 334 can have a terminal 324 at its distal end portion 326. Wire terminal 324 can have an opening for slipping the terminal around set screw 318. Wire terminal 324 can be secured to set screw 318 by fastener 322, for example, a nut. As fastener 322 is tightened, wire terminal 324 contacts set screw 318, providing electrical connectivity. Wire 334 includes an appropriate insulative sheath but for at its distal end portion 326 where terminal 324 contacts screw 318. Thus, the conductive surface of terminal 324 engages with the conductive surface of screw 318, thereby forming an electrical connection. In some embodiments, as shown in FIG. 8B, the wire terminal 324 and screw 318 on the outside of adaptor body can be covered by an insulating material 325 to prevent a user from coming into electrical contact with the conductive surfaces of screw 318 and terminal 324.

As illustrated in FIGS. 10, 11A, 11B, 12A, and 12B, to use a catheter system 10 as described in its various embodiments, electrical adapter 300 is coupled to catheter 100 via a port connected to a lumen of catheter 100, for example, port 160, and energy source connector 336 (discussed above) is coupled to an energy source to energize electrical terminal 316.

Figure 11A:
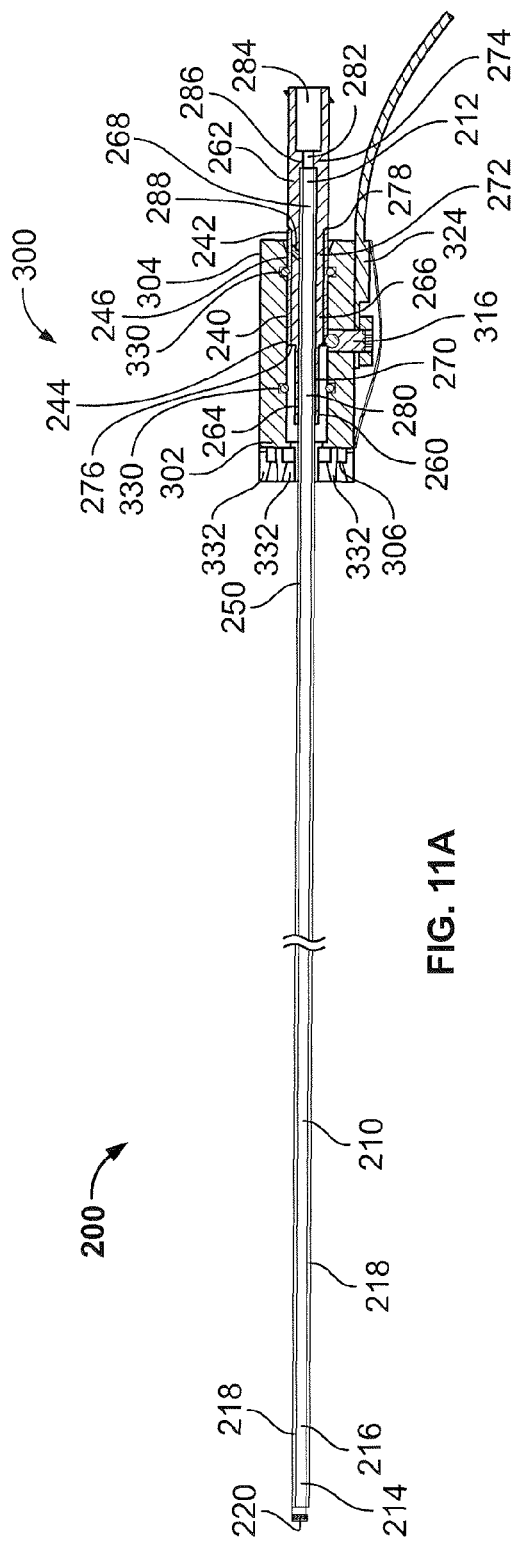
FIG. 11A illustrates a longitudinal cross-sectional view of the inner catheter inserted in the electrical adapter at a first position, according to an embodiment presented herein.

Distal tip 150 of catheter 100 can be inserted into a desired body lumen or cavity and navigated to a target location. Next, distal end portion 214 of elongated body 210 can be inserted into proximal end portion 310 of a channel 308 of electrical adapter body 302. Distal end portion 214 is advanced through channel 308 and into a lumen of catheter 100 via a port coupled to electrical adapter 300. Electrical connector 240 is isolated (does not contact) electrical terminal 316 while distal end portion 214 of elongated body 210 is within the lumen of catheter 100. Once distal end portion 214 of elongated body 210 is advanced to a first position at which the distal end portion 214 exits an opening at distal tip 150 of the lumen of catheter 100 (see FIG. 12A), distal end portion 244 of electrical connector 240 contacts electrical terminal 316, as illustrated in FIG. 11A, energizing electrical connector 240 which thereby energizes tool 220 which is electrically connected thereto. In some embodiments, tool 220 coupled to distal end portion 214 of elongated body 210 is from about 6 mm to about 26 mm away from distal tip 150 of first catheter 100 at the first position. However, the distance between tool 220 and distal end 150 can vary depending on the application. Advantageously, tool 220 coupled to distal end portion 214 is not energized until it exits the lumen of first catheter 100. Accidental activation of tool 220 while it is inside a lumen of catheter 100 is prevented because electrical terminal 316 is isolated from (does not contact) electrical connector 340 while tool 220 is inside the lumen of catheter 100.

Figure 10:
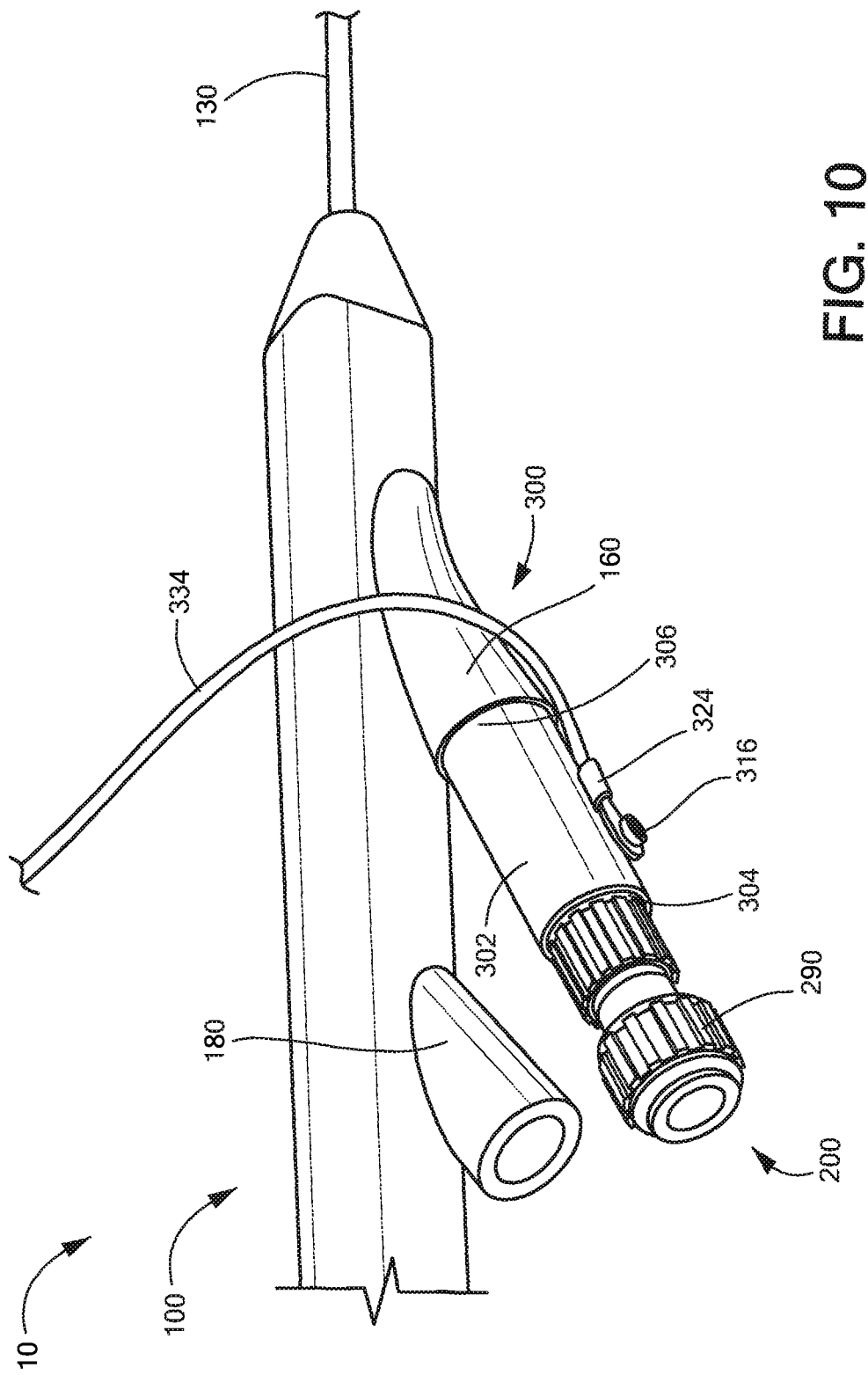
FIG. 10 illustrates a perspective view of a catheter system with the inner catheter fully inserted, according to an embodiment presented herein.
Figure 11B:
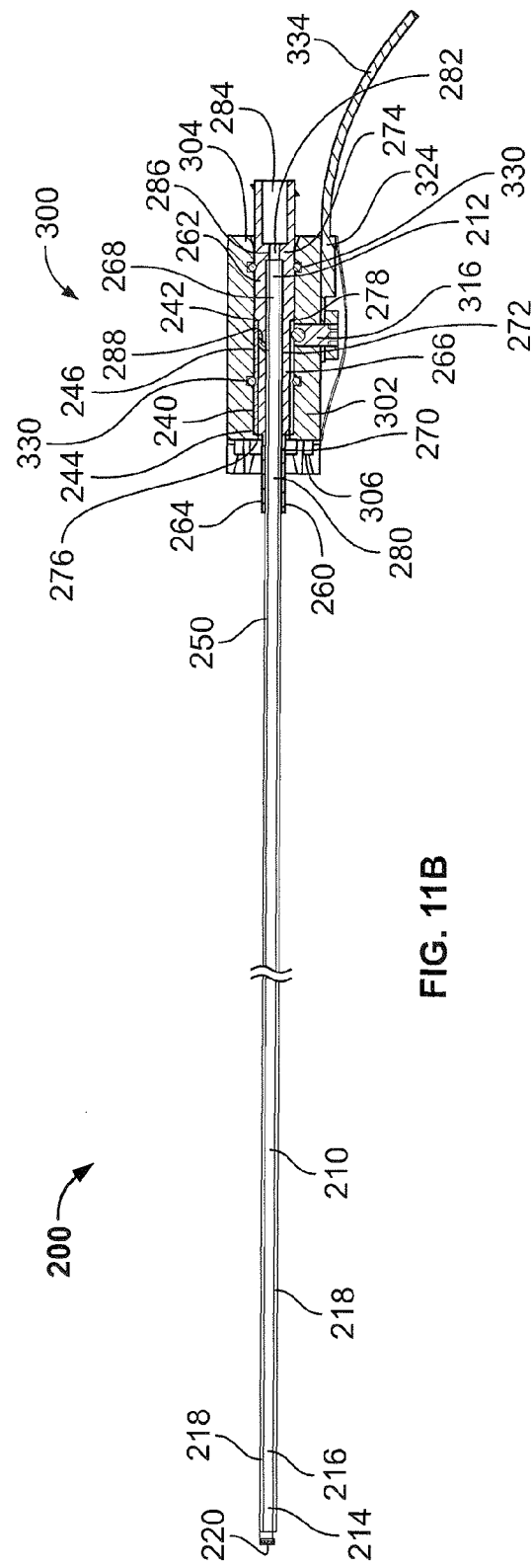
FIG. 11B illustrates a longitudinal cross-sectional view of the inner catheter inserted in the electrical adapter at a second position according to an embodiment presented herein.
Figure 12A:
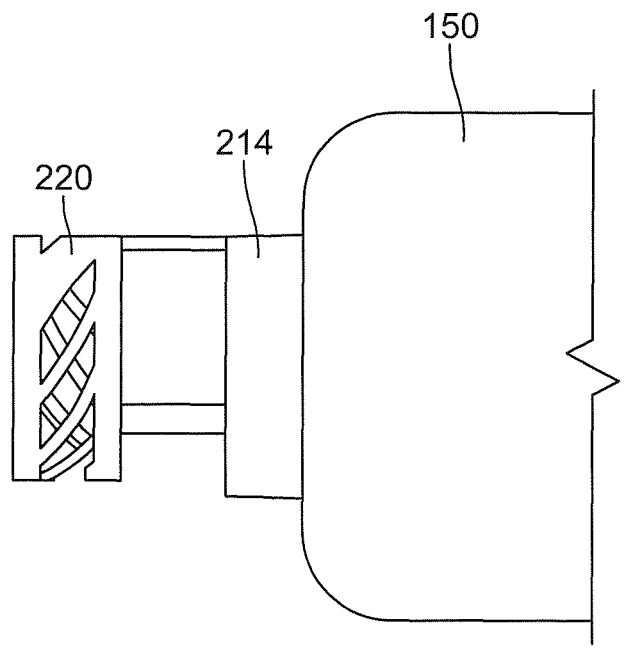
FIG. 12A illustrates a side view of the distal end portion of the inner catheter at the first position extending from the outer catheter according to an embodiment herein.
Figure 12B:
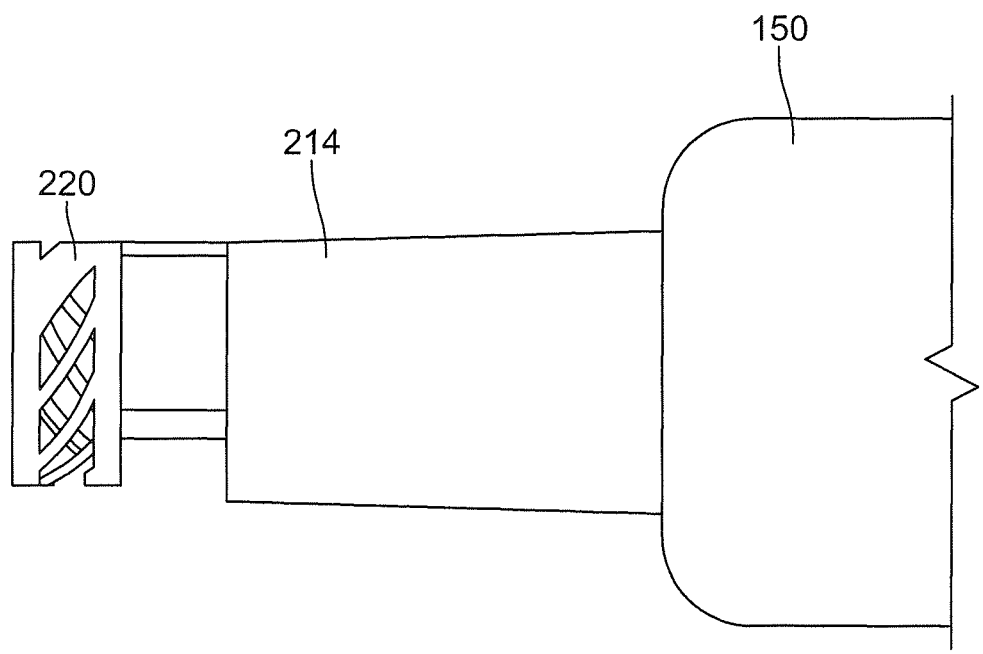
FIG. 12B illustrates a side view of the distal end portion of the inner catheter at the second position extending from the outer catheter according to an embodiment herein.

From the first position, distal end portion 214 can be further advanced in the distal direction to a second position as illustrated in FIGS. 10, 11B, and 12B. As distal end portion 214 is advanced to the second position, electrical connector 240 continues to contact electrical terminal 316 disposed in channel 308 of electrical adapter body 302 as illustrated in FIG. 11B, and distal end portion 214 advances further from distal tip 150 as shown in FIG. 12B. In some embodiments, tool 220 can be navigated by articulating distal end portion 214 at the second position. For example, once distal end portion 244 of electrical connector 240 passes distally, ball bearing 320 is forced radially away from the center of channel 308 by outer surface 246 of electrical connector 240; however, because ball bearing 320 is biased towards the center of channel 308, ball bearing 320 maintains contacts with outer surface 246 as catheter 200 advances.

In some embodiments, the second position electrical connector 340 is a predetermined distance, or stroke away, from the first position. The predetermined distance between the first position and the second can be determined by the longitudinal length of a portion of electrical connector 340 that forms the outermost periphery of catheter 200. In some embodiments, at the second position, the distal end of electrical connector 340 has advanced to the distal end of channel 308 and cannot be advanced further. For example, channel 308 can include a tapered inner diameter (see, e.g. FIG. 8D) at its distal portion 312 which connects with a lumen of catheter 100, and this tapered diameter can be larger than the outer diameter of electrical connector 340, thereby preventing further travel by electrical connector at the end of the stroke. In some embodiments, the stroke between the first and second positions is from about 6 to about 25 mm. The stroke, however, may be smaller or larger than this range depending on the application. Thus, the depth of distal end portion 214 within the body can be adjusted using the stroke, and can also be adjusted by adjusting the depth of distal tip 150 of catheter 100 in the body.

Anytime catheter 200 is at or between the first and second positions, tool 220 is energized and can treat tissue at a target location. For example, if tool 220 is an electrosurgical cutting tip, RF power can be applied to the cutting tip, and tissue at the target location can be cored by mechanical manipulation of a cutting edge on cutting tip 220. Mechanical manipulation occurs with motion in the distal direction and articulation of cutting portion 220. Cored tissue can then be aspirated via a lumen within elongated body 210, for example, central lumen 216 and aspiration holes 211.

In some embodiments having an electrosurgical cutting tip, catheter 100 and catheter 200 can be highly articulatable, for example, by using navigation wires in one or more lumens of catheter 200, or in lumen(s) of catheter 100. In some embodiments, as earlier noted, catheter 200 can be provided with a distal end portion formed from one or more coaxial segments of different durometer to support various ranges of articulation in response to manipulation by the navigation wire. Such articulation can allow a cutting tip more degrees of freedom for cutting tissue at a target location and can allow better control around a contour than can be achieved with conventional catheters that use a straight-line laser or argon beam.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. For example, in some embodiments, the bronchoscope-compatible catheters as described herein can be modified to include a laser tool on the tip for laser surgical procedures, in which the laser tip is selectively energized via an electrical adaptor. In some embodiments, for example, the outer catheter, such as an endoscope, can be manufactured to include the electrical adaptor such that the electrical adaptor is integral with the outer catheter (rather than being removably connected to the outer catheter). Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A catheter system comprising:
an electrical adapter including a hollow adapter body having a longitudinally extending channel and an electrical terminal positioned within the longitudinally extending channel, the electrical adapter being configured to be electrically connected to an energy source; and
a catheter having a longitudinal length and being removeably insertable within the electrical adapter, the catheter including an elongated body having a proximal end portion and a distal end portion, the distal end portion defining a first diameter and including an electrosurgical cutting tip, the distal end portion being configured to be inserted into a proximal most end of the longitudinally extending channel and advanced through an entirety of the longitudinally extending channel during an electrosurgical procedure; and
an electrical connector coupled to the proximal end portion of the elongated body, the electrical connector forming an outer periphery of the catheter along a portion of the longitudinal length of the catheter, the electrical connector defining a second diameter larger than the first diameter, the electrical connector configured to be inserted in the channel of the hollow adapter body, wherein the electrical terminal and the electrical connector are configured to be electrically connected to each other when the electrical connector is advanced to an electrical contact position within the channel, and are configured to be electrically isolated from each other when the electrical connector is proximal of the electrical contact position.

2. The catheter system of claim 1, wherein the electrical terminal comprises an exposed, electrically conductive surface biased towards a center of the longitudinally extending channel of the hollow adapter body.

3. The catheter system of claim 2, wherein the electrically conductive surface comprises a ball bearing.

4. The catheter system of claim 2, wherein the electrically conductive surface is configured to engage an electrically conductive surface of the electrical connector when the electrical connector is advanced to the electrical contact position within the longitudinally extending channel.

5. The catheter system of claim 4, wherein the electrical contact position includes a region from a first position to a second position, wherein the electrically conductive surface of the electrical terminal is configured to engage the electrically conductive surface of the electrical connector while the distal end of the electrical connector is advanced distally from the first position to the second position.

6. The catheter system of claim 1, further comprising a second catheter having a longitudinal length, the second catheter including an elongated body having a proximal end portion, a distal end portion, and a lumen extending from the proximal end portion to the distal end portion of the elongated body of the second catheter, the lumen of the second catheter extending distally from a distal end of the longitudinally extending channel of the electrical adapter, wherein at least a portion of the catheter is configured to be disposed within the lumen of the second catheter.

7. The catheter system of claim 6, wherein the distal end of the catheter exits an opening at a distal end of the lumen of the second catheter at the electrical contact position.

8. The catheter system of claim 6, wherein the second catheter is a bronchoscope.

9. The catheter system of claim 1, wherein the catheter has one or more aspiration holes on its sidewall at distal end portion of the catheter.

10. The catheter system of claim 1, wherein the electrosurgical cutting tip is electrically connected to the electrical connector.

11. A method comprising:
inserting a distal end of an inner catheter having a first diameter into a proximal most end of a channel defined by a hollow electrical adapter body; and
advancing the distal end of the inner catheter through the channel, through a lumen of an outer catheter that extends distally from a distal end of the channel of the hollow electrical adapter body, and to a first position at which the distal end of the inner catheter exits an opening at a distal end of the lumen of the outer catheter;
wherein, when the distal end of the inner catheter is advanced to the first position, an electrical terminal, which is disposed in the channel of the hollow electrical adapter body and electrically connected to an energy source, contacts an electrical connector on a proximal end portion of the inner catheter and having a second diameter larger than the first diameter, and electrically connects the electrical connector to the energy source, wherein when the distal end of the inner catheter is proximal of the first position, the electrical terminal fails to contact the electrical connector and electrically connect the electrical connector to the energy source.

12. The method of claim 11, wherein the advancing includes advancing distally the distal end of the inner catheter a distance from the first position to a second position, wherein the electrical connector on the proximal end portion of the inner catheter contacts the electrical terminal disposed in the channel of the hollow electrical adapter body as the distal end of the inner catheter is advanced along a distance from the first position to the second position.

13. The method of claim 12, wherein the distal end of the inner catheter includes a tool electrically connected to the electrical connector, wherein the tool is energized with electrical energy from the energy source when the distal end of the inner catheter is advanced to the first position and when the distal end of the inner catheter is advanced from the first position to the second position.

14. The method of claim 13, wherein the tool is an electrosurgical cutting tip; and
wherein the method further comprises:
introducing the distal ends of the inner and outer catheters into a body lumen; and
treating target tissue with the energized electrosurgical cutting tip.

* * * * *